United States Patent
Banowski et al.

(10) Patent No.: US 7,294,330 B2
(45) Date of Patent: Nov. 13, 2007

(54) β-GLUCURONIDASE INHIBITORS FOR USE IN DEODORANTS AND ANTIPERSPIRANTS

(75) Inventors: Bernhard Banowski, Duesseldorf (DE); Daniele Hoffmann, Duesseldorf (DE); Armin Wadle, Erkrath (DE); Petra Siegert, Haan (DE); Andrea Saettler, Duesseldorf (DE); Thomas Gerke, Neuss (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 737 days.

(21) Appl. No.: 10/838,930

(22) Filed: May 4, 2004

(65) Prior Publication Data

US 2004/0234466 A1    Nov. 25, 2004

Related U.S. Application Data

(63) Continuation of application No. PCT/EP02/11981, filed on Oct. 26, 2002.

(30) Foreign Application Priority Data

Nov. 6, 2001   (DE)   ............................... 101 54 368

(51) Int. Cl.
*A61Q 15/00*   (2006.01)
*A61K 36/00*   (2006.01)
*A61K 31/19*   (2006.01)
*A61K 8/02*    (2006.01)

(52) U.S. Cl. .................. 424/65; 424/400; 424/401; 424/725; 514/558

(58) Field of Classification Search .................. 424/65, 424/400, 401, 725; 514/557, 558
See application file for complete search history.

(56) References Cited

U.S. PATENT DOCUMENTS

| 3,542,919 A | 11/1970 | Buth et al. |
| 3,991,176 A | 11/1976 | Rubino |
| 5,643,559 A | 7/1997 | Eigen et al. |
| 5,676,937 A | 10/1997 | Eigen et al. |

FOREIGN PATENT DOCUMENTS

| DE | 1 165 574 | 3/1964 |
| DE | 197 56 454 C1 | 6/1999 |
| EP | 0 258 814 B1 | 4/1993 |
| EP | 0 586 235 B1 | 3/1997 |
| EP | 0 775 486 A1 | 5/1997 |
| FR | 2 342 725 | 9/1977 |
| FR | 2 394 290 | 1/1979 |
| FR | 2 727 014 A1 | 5/1996 |
| GB | 962 919 | 7/1964 |
| GB | 1 561 475 | 2/1980 |
| JP | 2001 002504 | 1/2001 |
| WO | WO 89/02264 A1 | 3/1989 |

OTHER PUBLICATIONS

Patent Abstracts of Japan, vol. 2000, No. 16 of JP 2001 002504 (2001).
D. Karentz et al., "Survey of mycosporine-like amino acid compounds in Antarctic marine organisms: potential protection from ultraviolet exposure", Marine Biology, vol. 108, pp. 157-166 (1991).

*Primary Examiner*—Shelley A. Dodson
(74) *Attorney, Agent, or Firm*—John E. Drach

(57) ABSTRACT

A non-therapeutic method for the inhibition of β-glucuronidase. Body odors result from the decomposition of steroid esters by β-glucuronidase. Specific β-glucuronidase-inhibiting compounds are disclosed.

19 Claims, No Drawings

β-GLUCURONIDASE INHIBITORS FOR USE IN DEODORANTS AND ANTIPERSPIRANTS

CROSS REFERENCE TO RELATED APPLICATIONS

This application is a continuation under 35 U.S.C. § 365(c) and 35 U.S.C. § 120 of international application PCT/EP02/11981, filed Oct. 26, 2002. This application also claims priority under 35 U.S.C. § 119 of DE 101 54 368.9, filed Nov. 6, 2001, which is incorporated herein by reference in its entirety.

BACKGROUND OF THE INVENTION

The invention relates to the non-therapeutic use of selected β-glucuronidase-inhibiting substances in a cosmetic deodorant or antiperspirant composition for reducing the body odor caused by decomposition of steroid esters.

Apocrine perspiration is a complex mixture which comprises, inter alia, steroids, cholesterol and other fats as well as approx. 10% of proteins. The decomposition products of apocrine perspiration, which substantially contribute towards body odor, in particular axillary body odor, can be divided into two classes, on the one hand short-chain, in particular $C_4$-$C_{10}$-fatty acids, which can be linear, branched, saturated and unsaturated, and on the other hand various steroid hormones and degradation products thereof. The metabolism products of androgens, in particular androstenol (5α-androst-16-en-3β-ol, 5α-androst-16-en-3α-ol) and androstenone (5α-androst-16-en-3-one), for example, are involved in typical body odor, especially in men.

Steroids themselves are not water-soluble. In order to be able to be transported away with body fluids, they are usually present in the form of sulfate or glucuronide. On the skin, cleavage of these steroid esters into the volatile free steroids takes place by means of hydrolytic enzymes of the skin bacteria, in particular the coryneform bacteria. All bacterial exoesterases are in principle capable of this, but especially the enzyme β-glucuronidase.

The deodorant compositions which are active according to the invention can intervene at this point and inhibit the activity of the bacterial exoesterases. They therefore differ from the purely bacteriostatic or bactericidal compositions of the prior art, which can have the disadvantage of impairing the naturally occurring microflora of the skin.

Combating body odor caused by steroids by inhibiting β-glucuronidase is known in the prior art, for example from the publications U.S. Pat. No. 5,643,559 and U.S. Pat. No. 5,676,937. However, with $Cu^{2+}$, zinc glycinate, hexametaphosphate, D-glucaro-δ-lactone, EDTA, NTA, orthophenanthroline and sodium sulfate, these documents disclose only a small number of β-glucuronidase-inhibiting active compounds.

The object of the present invention was to identify further β-glucuronidase-inhibiting active compounds in order to render possible a wider variability, flexibility and skin tolerability in the formulation of cosmetic deodorants. The identification of known cosmetic active compounds as β-glucuronidase inhibitors moreover renders possible a lowering of the dosage of these active compounds. The enzyme-inhibiting action often already manifests itself at low active compound concentrations at which no bacteriostatic or bactericidal action is yet found. It has been found, surprisingly, that the use of aryl-sulfatase inhibitors in deodorants is suitable, especially in men, for preventing the formation of body odor. It is possible here for the expert, in the context of his general technical knowledge, to coordinate the active compounds in the deodorant composition in respect of their amount and/or their nature to the particular user group in a sex-specific manner.

DESCRIPTION OF THE INVENTION

The present invention relates to the non-therapeutic use of at least one β-glucuronidase-inhibiting substance chosen from monobasic mono-α-hydroxycarboxylic acids having 2-6 carbon atoms and their physiologically acceptable salts, monobasic polyhydroxycarboxylic acids having 4-8 carbon atoms and 3-7 hydroxyl groups, their intramolecular condensation products as well as ethers thereof with mono-, oligo- and polysaccharides or esters thereof with organic and with inorganic acids as well as the physiologically acceptable salts of these components, polybasic carboxylic acids which are not hydroxy-substituted and have 3-8 carbon atoms and 2-3 carboxyl groups, their esters with optionally alkyl-substituted mono- and oligosaccharides as well as the physiologically acceptable salts of these components, polybasic monohydroxycarboxylic acids having 4-8 carbon atoms and 2-3 carboxyl groups, their esters with optionally alkyl-substituted mono- and oligosaccharides as well as the physiologically acceptable salts of these components, polybasic polyhydroxycarboxylic acids having 4-8 carbon atoms, 2-6 hydroxyl groups and 2-3 carboxyl groups, their esters with optionally alkyl-substituted mono- and oligosaccharides as well as the physiologically acceptable salts of these components, aromatic carboxylic acids having 6-20 carbon atoms, 1-2 phenyl radicals, 1-6 hydroxyl groups and 1 carboxyl group, as well as physiologically acceptable salts thereof, amino acids as well as physiologically acceptable salts thereof, 6,7-disubstituted 2,2-dialkylchromanes or -chromenes, phenolic glycosides with a phenoxy radical substituted at least in the para-position, wherein the substituents are chosen from a methoxy, ethoxy, isopropoxy, n-propoxy, vinyl, methylvinyl, 1-propenyl, 2-propenyl (allyl), isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, flavonoids, isoflavonoids, polyphenols, the extracts from green tea (*Camellia sinensis*), from Paraguayan tea (*Ilex paraguayensis*), from Japanese tea (*Camellia japanensis*), from the fruits (berries) of the fan palm or saw palm (*Saw Palmetto, Serenoa repens*), from the leaves of *Gingko biloba*, from apple pips, from the fruits (berries) of *Phyllanthus emblica*, from the leaves of the olive tree (*Olea europaea*), from the bark of the pine tree (*Pinus* Pinaster), from rosemary, from *Bacopa* Monniera, from willow-herb, hyssop, clove, from the blue alga *Spirulina platensis* which has been enriched with magnesium, and from yeast, monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, derivatives of phosphonic acid and phosphoric acid chosen from hydroxyethane-1,1-diphosphonic acid, diethylenetriaminepenta (methylenephosphonic acid), myo-inositol-hexaphosphoric acid (phytic acid) and phosphonomethylated chitosan as well as the alkali metal salts of these components, zinc ricinoleate, geraniol-7 EO as well as soluble inorganic salts of copper (II), zinc and magnesium, in a cosmetic deodorant or antiperspirant composition for reducing the body odor caused by hydrolytic decomposition of steroid esters.

The monobasic mono-α-hydroxycarboxylic acids having 2-6 carbon atoms which are preferred according to the invention include glycollic acid, lactic acid, α-hydroxybutyric acid, α-hydroxyvaleric acid and α-hydroxycaproic acid. Their physiologically acceptable salts are also preferred, in particular the zinc salts and the salts of the alkali metals, particularly preferably of sodium and potassium. Exceptionally preferred representatives are zinc lactate and potassium lactate. They are employed according to the invention in amounts of 0.01 to 5.0 wt. %, preferably 0.03 to 2.0 wt. % and particularly preferably 0.05 to 1.0 wt. %, in each case based on the total cosmetic composition.

The monobasic polyhydroxycarboxylic acids having 4-8 carbon atoms and 3-7 hydroxyl groups which are preferred according to the invention include gluconic acid, gulonic acid, 2-oxo-gulonic acid, glucoheptonic acid, galactonic acid, mannonic acid, fructonic acid, arabinonic acid, xylonic acid and ribonic acid. The intramolecular condensation products of this group of polyhydroxycarboxylic acids are also particularly suitable according to the invention, with ascorbic acid, 2-oxogulonic acid γ-lactone, as a particularly preferred representative. The ethers of ascorbic acid with mono-, oligo- and polysaccharides, the esters of ascorbic acid with organic and with inorganic acids as well as the physiologically acceptable salts of these components are furthermore preferred. Of the salts, the zinc, copper and manganese salts and the salts of the alkali metals and the alkaline earth metals are particularly preferred, especially those of sodium, potassium, magnesium and calcium. Suitable acid derivatives are zinc gluconate, copper gluconate, manganese gluconate and magnesium glucoheptonate. Suitable ascorbic acid derivatives are sodium ascorbyl phosphate, magnesium ascorbyl phosphate, ascorbyl palmitate, disodium ascorbyl phosphate, disodium ascorbyl sulfate, sodium ascorbate, magnesium ascorbate, ascorbyl stearate, ascorbyl dipalmitate, ascorbyl acetate, potassium ascorbyl tocopheryl phosphate, chitosan ascorbate and ascorbyl glucoside.

The monobasic polyhydroxycarboxylic acids or their derivatives are employed in amounts of 0.01 to 5.0 wt. %, preferably 0.05 to 2.0 and particularly preferably 0.1 to 1.0 wt. %, in each case based on the total cosmetic composition.

The polybasic carboxylic acids which are not hydroxy-substituted and have 3-8 carbon atoms and 2-3 carboxyl groups and are preferred according to the invention, their esters with optionally alkyl-substituted mono- and oligosaccharides as well as the physiologically acceptable salts of these components include methylglycinediacetic acid and its mono-, di- and tri-alkali metal salts as well as sulfosuccinic acid and its mono-, di- and tri-alkali metal salts.

In particular, the esters of sulfosuccinic acid and of mono- and di-alkali metal sulfosuccinate with alkyl-substituted mono- and oligosaccharides are also suitable as β-glucuronidase inhibitors. The alkyl-substituted mono- and oligosaccharides are preferably chosen from glucose or oligoglucose, having an average degree of oligomerization of 1.1 to 2.0, etherified with a $C_6$-$C_{18}$-alkanol or with technical-grade mixtures of $C_6$-$C_{18}$-alkanols. Such compounds are described e.g. in the publication EP 258 814 B1. Disodium coconut alkyl polyglucoside sulfosuccinate (Disodium Cocopolyglucose Sulfosuccinate, obtainable as the commercial product Eucarol® AGE SS from Cesalpinia Chemicals) is particularly preferred.

The polybasic carboxylic acids which are not hydroxy-substituted or their derivatives are employed in amounts of 0.01 to 10.0 wt. %, preferably 0.05 to 5.0 and particularly preferably 0.1 to 2.0 wt. %, in each case based on the total cosmetic composition.

The polybasic monohydroxycarboxylic acids having 4-8 carbon atoms and 2-3 carboxyl groups which are preferred according to the invention, their esters with optionally alkyl-substituted mono- and oligosaccharides and the physiologically acceptable salts of these components include citric acid, malic acid (hydroxysuccinic acid), hydroxymaleic acid, hydroxyglutaric acid, hydroxyadipic acid, hydroxypimelic acid and hydroxyazelaic acid, $C_8$-$C_{18}$-alkyl (oligo-)glucoside esters thereof and the mono-, di- and tri-alkali metal salts and the aluminum salts of these components. Particularly preferred polybasic monohydroxycarboxylic acids are citric acid and malic acid as well as derivatives thereof. Citric acid, sodium citrate, tripotassium citrate, aluminum citrate and citric acid esters of glucose or oligoglucose, having an average degree of oligomerization of 1.1 to 2.0, which are etherified with a $C_6$-$C_{18}$-alkanol or with technical-grade mixtures of $C_6$-$C_{18}$-alkanols, as well as mono- and di-alkali metal salts thereof are very particularly preferred. Such compounds are described e.g. in the publication EP 258 814 B1. Disodium coconut alkyl polyglucoside citrate (Disodium Cocopolyglucose Citrate, obtainable as the commercial product Eucarol® AGE EC from Cesalpinia Chemicals) is particularly preferred.

The polybasic monohydroxycarboxylic acids having 4-8 carbon atoms and 2-3 carboxyl groups or their derivatives are employed in amounts of 0.01 to 10.0 wt. %, preferably 0.05 to 5.0 and particularly preferably 0.1 to 2.0 wt. %, in each case based on the total cosmetic composition.

The polybasic polyhydroxycarboxylic acids having 4-8 carbon atoms, 2-6 hydroxyl groups and 2-3 carboxyl groups which are preferred according to the invention, their esters with optionally alkyl-substituted mono- and oligosaccharides and the physiologically acceptable salts of these components include erythraric acid (meso-tartaric acid), L-threaric acid ((+)-tartaric acid), D(−)-tartaric acid, DL-tartaric acid (racemic tartaric acid), glucaric acid, galactaric acid (mucic acid), mannaric acid, fructaric acid, arabinaric acid, xylaric acid and ribaric acid, $C_8$-$C_{18}$-alkyl (oligo-) glucoside esters thereof and the mono-, di- and tri-alkali metal salts of these components. Particularly preferred polybasic polyhydroxycarboxylic acids are tartaric acid, in particular naturally occurring (+)-tartaric acid (L-threaric acid) and DL-tartaric acid, and furthermore galactaric acid as well as derivatives thereof.

The tartaric acid esters of glucose or oligoglucose having an average degree of oligomerization of 1.1 to 2.0 which are etherified with a $C_6$-$C_{18}$-alkanol or with technical-grade mixtures of $C_6$-$C_{18}$-alkanols, as well as mono- and di-alkali metal salts thereof are also particularly preferred. Such compounds are described e.g. in the publication EP 258 814 B1. Disodium coconut alkyl polyglucoside tartrate (Disodium Cocopolyglucose Tartrate, obtainable as the commercial product Eucarol® AGE ET from Cesalpinia Chemicals) is particularly preferred.

The polybasic polyhydroxycarboxylic acids having 4-8 carbon atoms, 2-6 hydroxyl groups and 2-3 carboxyl groups or their derivatives are employed in amounts of 0.01 to 10.0 wt. %, preferably 0.05 to 5.0 and particularly preferably 0.1 to 2.0 wt. %, in each case based on the total cosmetic composition.

The aromatic carboxylic acids having 6-20 carbon atoms, 1-2 phenyl radicals, 1-6 hydroxyl groups and 1 carboxyl group which are preferred according to the invention and derivatives thereof include mandelic acid, para-hydroxymandelic acid, rosemary acid, ferulic acid, chlorogenic acid, salicylic acid, 2,3-dihydroxybenzoic acid (pyrocatechic acid), 2,4-dihydroxybenzoic acid (β-resorcylic acid), 2,5- dihydroxybenzoic acid (gentisic acid), 2,6-dihydroxybenzoic acid (γ-resorcylic acid), 3,4-dihydroxybenzoic acid (protocatechuic acid), 3,5-dihydroxybenzoic acid (α-resorcylic acid), gallic acid, the methyl, ethyl isopropyl, propyl, butyl, hexyl, ethylhexyl, octyl, decyl, ethyloctyl, cetyl and stearyl esters and the alkali metal salts of these carboxylic acids. Rosemary acid, ferulic acid and para-hydroxymandelic acid sodium salt are particularly preferred.

The aromatic carboxylic acids having 6-20 carbon atoms, 1-2 phenyl radicals, 1-6 hydroxyl groups and 1 carboxyl group or their derivatives are employed in amounts of 0.001 to 10 wt. %, preferably 0.005 to 5 and particularly preferably 0.008 to 2 wt. %, in each case based on the total cosmetic composition.

The amino acids which are preferred according to the invention and physiologically acceptable salts thereof include the mycosporine-like amino acids (MAA) which can be isolated from marine organisms, as well as glycine, serine, tyrosine, threonine, cysteine, asparagine, glutamine, pyroglutamic acid, alanine, valine, leucine, isoleucine, proline, tryptophan, phenylalanine, methionine, aspartic acid, glutamic acid, lysine, arginine and histidine as well as the zinc salts and the acid addition salts of the amino acids mentioned.

The mycosporine-like amino acids (Mycosporine-like Amino Acids, MAA) which are obtainable from marine organisms are particularly preferred as β-glucuronidase inhibitors. An overview of MAA is given, for example, by D. Karentz et al., Marine Biology 108, 157-166, 1991. Mycosporine is the generic name for water-soluble, UV-absorbing metabolism products of, for example, fungi, algae and *Cyanobacteria*, the molecules of which contain a cyclohexenone chromophore conjugated with the amino group of an amino acid or of an amino alcohol. The mycosporine-like amino acids which are contained in marine organisms are iminocarbonyl derivatives of the mycosporine-cyclohexenone chromophore.

MAA are sensitive to hydrolysis, and they are therefore preferably employed in anhydrous compositions. Further particularly preferred amino acids and derivatives are glycine, pyroglutamic acid, phenylalanine, arginine as well as zinc glycinate, zinc glycinate monohydrate, zinc pyroglutamate and arginine hydrochloride.

According to the invention, the amino acids are employed in amounts of 0.001 to 2 wt. %, preferably 0.01 to 1 wt. % and particularly preferably 0.02 to 0.5 wt. %, in each case based on the total cosmetic composition.

In a further preferred embodiment, the β-glucuronidase inhibitors used according to the invention are chosen from 6,7-disubstituted, 2,2-dialkylchromanes or -chromenes of the general formulae (I) or (II)

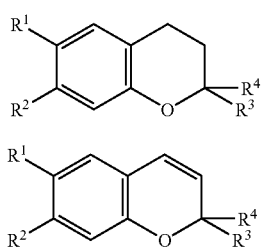

wherein $R^1$ and $R^2$ independently of one another represent an OH group, a methoxy group or a $CF_3CH_2O$ group and $R^3$ and $R^4$ independently of one another represent a $C_1$-$C_4$-alkyl group.

The substituents $R^1$ and $R^2$ independently of one another are chosen from an OH group, a methoxy group and a $CF_3CH_2O$ group. In a preferred embodiment, $R^1$ and $R^2$ independently of one another are chosen from an OH group and a methoxy group. In a particularly preferred embodiment, $R^1$ represents an OH group and $R^2$ represents a methoxy group.

The substituents $R^3$ and $R^4$ independently of one another represent a $C_1$-$C_4$-alkyl group. $C_1$-$C_4$-Alkyl group here is to be understood according to the invention as meaning a methyl, ethyl, n-propyl, isopropyl, n-butyl, isobutyl or 2-methylpropyl, sec-butyl or 1-methyipropyl or a tert-butyl group. In a preferred embodiment, $R^3$ and $R^4$ independently of one another are chosen from a methyl, ethyl, n-propyl, isopropyl and an n butyl group. Particularly preferably, $R^3$ and $R^4$ independently of one another represent a methyl or ethyl group. It is exceptionally preferable for $R^3$ and $R^4$ to be identical.

The 6,7-disubstituted 2,2-dialkylchromanes are preferably used according to the invention. An active compound which is exceptionally preferably used according to the invention is 2,2-dimethyl-6-hydroxy-7-methoxy-chromane with the systematic name 3,4-dihydro-7-methoxy-2,2-dimethyl-2H-1-benzopyran-6-ol and the INCI name Dimethylmethoxy Chromanol. The substance is obtainable under the commercial name Lipochroman-6 from Lipotec S.A.

The 6,7-disubstituted 2,2-dialkylchromanes or -chromenes of the general formulae (I) or (II) are employed according to the invention in amounts of 0.001-5 wt. %, preferably 0.005-2 wt. % and particularly preferably 0.01-1 wt. %, in each case based on the total cosmetic composition.

Phenolic glycosides having a phenoxy radical substituted at least in the para-position, wherein the substituents are chosen from a methoxy, ethoxy, isopropoxy, n-propoxy, vinyl, methylvinyl, 1-propenyl, 2-propenyl (allyl), isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, which are particularly preferred according to the invention are 2-methoxy-4-(2-propenyl)phenyl β-D-glucoside (eugenyl glucoside) and 4-(γ-ketobutyl)phenyl β-D-glucoside (raspberry ketone glucoside).

According to the invention, these components are employed in amounts of 0.001 to 3 wt. %, preferably 0.01 to 2 wt. % and particularly preferably 0.02 to 1 wt. %, in each case based on the total cosmetic composition.

In a further preferred embodiment, the β-glucuronidase inhibitors used according to the invention are chosen from extracts from green tea (*Camellia sinensis*) Paraguayan tea (*Ilex paraguayensis*), Japanese tea (*Camellia japanensis*), from the fruits (berries) of the fan palm or saw palm (Saw Palmetto, *Serenoa repens*), from the leaves of *Gingko biloba*, from apple pips, from the fruits (berries) of *Phyllanthus emblica*, from the leaves of the olive tree (*Olea europaea*), from the bark of the pine tree (*Pinus* Pinaster) from rosemary, from *Bacopa* Monniera, from willow-herb, hyssop, clove, from the blue alga *Spirulina platensis* which has been enriched with magnesium, as well as from yeast.

According to the invention, the plant and yeast extracts are employed in amounts of 0.001 to 20 wt. %, preferably 0.005 to 10 and particularly preferably 0.01 to 5 wt. % of active substance, in each case based on the total cosmetic composition.

Since the plant extracts which are suitable according to the invention comprise flavonoids, flavonoids are also disclosed explicitly as β-glucuronidase inhibitors which are suitable and preferred according to the invention.

The flavonoids which are preferred according to the invention include the glycosides of flavones, of flavanones, of 3-hydroxyflavones (flavonols), of aurones and of isoflavones. Particularly preferred flavonoids are chosen from naringin (aurantiin, naringenin 7-rhamnoglucoside), α-glucosylrutin, α-glucosylmyricetin, α-glucosylisoquercetin, α-glucosylquercetin, hesperidin (3',5,7-trihydroxy-4'-methoxyflavanone 7-rhamnoglucoside, hesperitin 7-O-rhamnoglucoside), neohesperidin, rutin (3,3',4',5,7-pentahydroxyflavone 3-rhamnoglucoside, quercetin 3-rhamnoglucoside), troxerutin (3,5-dihydroxy-3',4',7-tris(2-hydroxyethoxy)-flavone 3-(6-O-(6-deoxy-α-L-mannopyranosyl)-β-D-glucopyranoside)), monoxerutin (3,3',4',5-tetrahydroxy-7-(2-hydroxyethoxy)-flavone 3-(6-O-(6-deoxy-α-L-mannopyranosyl)-β-D-glucopyranoside)), diosmin (3',4',7-trihydroxy-5-methoxyflavanone 7-rhamnoglucoside), eriodictin and apigenin 7-glucoside (4',5,7-trihydroxyflavone 7-glucoside).

The biflavonoids built up from two flavonoid units, which occur e.g. in Gingko species, are also preferred. Further preferred flavonoids are the chalcones, above all phloricin and neohesperidin dihydrochalcone.

Naringin and apigenin 7-glucoside are flavonoids which are particularly preferred according to the invention.

According to the invention, the flavonoids are employed in amounts of 0.001 to 1 wt. %, preferably 0.005 to 0.5 wt. % and particularly preferably 0.01 to 0.4 wt. %, in each case based on the flavonoid active substance in the total cosmetic composition.

In a further preferred embodiment, the β-glucuronidase inhibitors used according to the invention are chosen from isoflavonoids, the isoflavones and the isoflavones glycosides being included among these.

In the context of the present invention, isoflavones are to be understood as meaning substances which are hydrogenation, oxidation or substitution products of 3-phenyl-4H-1-benzopyran, wherein a hydrogenation can be present in the 2,3-position of the carbon skeleton, an oxidation can be present in the 4-position, with the formation of a carbonyl group, and substitution is to be understood as meaning the replacement of one or more hydrogen atoms by hydroxyl or methoxy groups. The isoflavones according to the invention include, for example, daidzein, genistein, prunetin, biochanin, orobol, santal, pratensein, irigenin, glycitein, biochanin A and formononetin. Daidzein, genistein, glycitein and formononetin are preferred isoflavones.

In the isoflavone glycosides used according to the invention, the isoflavones are linked glycosidically with at least one sugar via at least one hydroxyl group. Possible sugars are mono- or oligosaccharides, in particular D-glucose, G-galactose, D-glucuronic acid, D-galacturonic acid, D-xylose, D-apiose, L-rhamnose, L-arabinose and rutinose. Preferred examples of the isoflavone glycosides used according to the invention are daidzin and genistin.

It is furthermore preferable according to the invention if the isoflavones and/or glycosides thereof are contained in the formulations as constituents of a substance mixture obtained from a plant, in particular a plant extract. Such plant substance mixtures can be obtained in the manner familiar to the expert, for example by pressing out or extraction from plants, such as soya, red clover or chick peas. Isoflavones or isoflavone glycosides in the form of extracts obtained from soya, such as are commercially obtainable, for example, under the product name Soy Protein Isolate SPI (Protein Technology International, St. Louis) or Soy Phytochemicals Concentrate SPC (Archer Daniels Midland, Decatur) are particularly preferably employed in the formulations according to the invention.

According to the invention, the isoflavonoids are employed in amounts of 0.001 to 1 wt. %, preferably 0.005 to 0.5 wt. % and particularly preferably 0.01 to 0.4 wt. %, in each case based on the isoflavonoid active substance in the total cosmetic composition.

Since the plant extracts which are suitable according to the invention comprise polyphenols, polyphenols are also disclosed explicitly as β-glucuronidase inhibitors which are suitable and preferred according to the invention.

According to the invention, polyphenols are to be understood as meaning aromatic compounds which contain at least two phenolic hydroxyl groups in the molecule. These include the three dihydroxybenzenes pyrocatechol, resorcinol and hydroquinone, and furthermore phloroglucinol, pyrogallol and hexahydroxybenzene. In nature, free and etherified polyphenols occur, for example, in flower pigments (anthocyanidines, flavones), in tanning substances (catechols, tannins), as lichen or fern constituents (usnic acid, acylpolyphenols), in lignins and as gallic acid derivatives, Preferred polyphenols are flavones, catechols, usnic acid and, as tannins, the derivatives of gallic acid, digallic acid and digalloylgallic acid. Particularly preferred polyphenols are the monomeric catechols, that is to say the derivatives of flavan-3-ols, and leucoanthocyanidines, that is to say the derivatives of leucoanthocyanidines which preferably carry phenolic hydroxyl groups in the 5,7,3',4',5'-position, preferably epicatechol and epigallocatechol, as well as the tanning substances formed therefrom by self-condensation. Such tanning substances are preferably employed not in the isolated pure substance but as extracts of plant parts rich in tanning substances, e.g. extracts of catechu, quebracho, oak bark and pine bark as well as other tree barks, leaves of green tea (*camellia sinensis*) and Paraguayan tea. The tannins are also particularly preferred.

According to the invention, the polyphenols are employed in amounts of 0.001 to 10 wt. %, preferably 0.005 to 5 wt. % and particularly preferably 0.01 to 3 wt. %, in each case based on the total cosmetic composition.

The monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, which are preferred according to the invention include phenoxyethanol, 2-phenylethyl alcohol, 5-hydroxy-2-(hydroxymethyl)-4-pyrone (kojic acid), 5-methyl-2-(1-methylvinyl)cyclohexan-1-ol (isopulegol) and 2-hydroxy-4-isopropyl-2,4,6-cycloheptatrien-1-one (hinokitiol).

Phenoxyethanol and 2-phenylethyl alcohol are employed according to the invention in amounts of 0.1 to 10 wt. %, preferably 0.3 to 5.0 and particularly preferably 0.5 to 2.0 wt. %, in each case based on the total cosmetic composition.

Kojic acid, isopulegol and hinokitiol are employed according to the invention in amounts of 0.0001 to 5 wt. %, preferably 0.0005 to 3-wt. % and particularly preferably 0.005 to 0.5 wt. %, in each case based on the total cosmetic composition.

In a further preferred embodiment, the phosphonic acid and phosphoric acid derivatives used according to the invention are chosen from hydroxyethane-1,1-diphosphonic acid (etidronic acid), diethylenetriamine-penta(methylenephosphonic acid), myo-inositol-hexaphosphoric acid (phytic acid) and phosphonomethylated chitosan as well as the alkali metal salts of these components. The sodium salts are particularly preferred. Etidronic acid and diethylenetriaminepenta-(methylenephosphonic acid) as well as alkali metal salts thereof are employed according to the invention in amounts of 0.01 to 5.0 wt. %, preferably 0.05 to 3.0 and particularly preferably 0.1 to 2.0 wt. %, in each case based on the total cosmetic composition.

Phytic acid and phosphonomethylated chitosan as well as alkali metal salts thereof are employed according to the invention in amounts of 0.01 to 10 wt. %, preferably 0.05 to 5 wt. % and particularly preferably 0.25 to 2 wt. %, in each case based on the total cosmetic composition.

In a further preferred embodiment, zinc ricinoleate is used as the β-glucuronidase inhibitor in amounts of 0.01-1, preferably 0.05-0.5, particularly preferably 0.1-0.3 wt. %, in each case based on the total composition.

In a further preferred embodiment, geraniol-7 EO, the ethylene oxide adduct of (2E)-3,7-dimethyl-2,6-octadien-1-ol having an average degree of ethoxylation of 7, is used as the β-glucuronidase inhibitor.

Geraniol-7 EO is employed according to the invention in amounts of 0.0001 to 5 wt. %, preferably 0.0005 to 3 wt. % and particularly preferably 0.005 to 2 wt. %, in each case based on the total cosmetic composition.

Soluble inorganic salts of copper(II), zinc and magnesium, for example $CuCl_2 \cdot 5 H_2O$, $CuSO_4 \cdot 5 H_2O$, zinc sulfate and magnesium chloride, are also suitable as the β-glucuronidase inhibitor. The inorganic salts which are suitable according to the invention are employed in amounts of 0.00001 to 1 wt. %, preferably 0.0001 to 0.5 and particularly preferably 0.0005 to 0.2 wt. %, in each case based on the total cosmetic composition.

The present invention also relates to a non-therapeutic method of reducing body odor by means of inhibition of β-glucuronidase on the skin, which is characterized in that a cosmetic deodorant or antiperspirant composition comprising at least one β-glucuronidase-inhibiting substance chosen from monobasic mono-α-hydroxycarboxylic acids having 2-6 carbon atoms and their physiologically acceptable salts, monobasic polyhydroxycarboxylic acids having 4-8 carbon atoms and 3-7 hydroxyl groups, their intramolecular condensation products as well as ethers thereof with mono-, oligo- and polysaccharides or esters thereof with organic and with inorganic acids as well as the physiologically acceptable salts of these components, polybasic carboxylic acids which are not hydroxy-substituted and have 3-8 carbon atoms and 2-3 carboxyl groups, their esters with optionally alkyl-substituted mono- and oligosaccharides as well as the physiologically acceptable salts of these components, polybasic monohydroxycarboxylic acids having 4-8 carbon atoms and 2-3 carboxyl groups, their esters with optionally alkyl-substituted mono- and oligosaccharides as well as the physiologically acceptable salts of these components, polybasic polyhydroxycarboxylic acids having 4-8 carbon atoms, 2-6 hydroxyl groups and 2-3 carboxyl groups, their esters with optionally alkyl-substituted mono- and oligosaccharides as well as the physiologically acceptable salts of these components, aromatic carboxylic acids having 6-20 carbon atoms, 1-2 phenyl radicals, 1-6 hydroxyl groups and 1 carboxyl group, as well as physiologically acceptable salts thereof, amino acids as well as physiologically acceptable salts thereof, 6,7-disubstituted 2,2-dialkylchromanes or -chromenes, phenolic glycosides with a phenoxy radical substituted at least in the para-position, wherein the substituents are chosen from a methoxy, ethoxy, isopropoxy, n-propoxy, vinyl, methylvinyl, 1-propenyl, 2-propenyl (allyl), isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, flavonoids, isoflavonoids, polyphenols, the extracts from green tea (*Camellia sinensis*), Paraguayan tea (*Ilex paraguayensis*), Japanese tea (*Camellia japanensis*), from the fruits (berries) of the fan palm or saw palm (Saw Palmetto, *Serenoa repens*), from the leaves of *Gingko biloba*, from apple pips, from the fruits (berries) of *Phyllanthus emblica*, from the leaves of the olive tree (*Olea europaea*), from the bark of the pine tree (*Pinus* Pinaster), from rosemary, from *Bacopa* Monniera, from willow-herb, hyssop, clove, from the blue alga *Spirulina platensis* which has been enriched with magnesium, and from yeast, monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, derivatives of phosphonic acid and phosphoric acid chosen from hydroxyethane-1,1-diphosphonic acid, diethylenetriaminepenta (methylene phosphonic acid), myo-inositol-hexaphosphoric acid (phytic acid) and phosphonomethylated chitosan as well as the alkali metal salts of these components, zinc ricinoleate, geraniol-7 EQ as well as the soluble inorganic salts of copper(II), zinc and magnesium, is applied to the skin, in particular the skin of the armpits.

In a preferred embodiment, the non-therapeutic method for reducing body odor by means of β-glucuronidase-inhibiting substances is characterized in that it is employed on men.

The cosmetic deodorant or antiperspirant compositions which comprise the β-glucuronidase inhibitors used according to the invention can be in the form of a powder, in stick form, in the form of an aerosol spray, pump spray, liquid and gelatinous roll on application, cream, gel and in the form of an impregnated flexible substrate.

Deodorant or antiperspirant sticks can be in the gelled form, on an anhydrous wax basis and on the basis of W/O emulsions and O/W emulsions. Gel sticks can be produced on the basis of fatty acid soaps, dibenzylidenesorbitol, N-acylamino acid amides, 12-hydroxystearic acid and other gel-forming agents.

Aerosol sprays, pump sprays, roll on applications and creams can be in the form of a water-in-oil emulsion, oil-in-water emulsion, water-in-silicone oil emulsion, silicone oil-in-water emulsion, oil-in-water microemulsion, silicone oil-in-water microemulsion, anhydrous suspension, alcoholic and hydroalcoholic solution, aqueous gel and in the form of an oil. All the compositions mentioned can be thickened, for example on the basis of fatty acid soaps, dibenzylidenesorbitol, N-acylamino acid amides, 12-hydroxystearic acid, polyacrylates of the Carbomer and Carbopol type, polyacrylamides and polysaccharides, which can be chemically and/or physically modified.

The emulsions and microemulsions can be transparent, translucent or opaque.

The cosmetic deodorant or antiperspirant compositions which comprise the β-glucuronidase inhibitors used according to the invention can furthermore comprise fat substances. Fat substances are to be understood as meaning fatty acids, fatty alcohols, naturally occurring and synthetic cosmetic oil components and naturally occurring and synthetic waxes, which can be both in solid form and in liquid form in aqueous or oily dispersion. Fatty acids which can be employed are linear and/or branched, saturated and/or unsaturated $C_8$-$C_{30}$-fatty acids. $C_{10-22}$-Fatty acids are preferred. Examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid, as well as technical-grade mixtures thereof. The use of stearic acid is particularly preferred. The fatty acids employed can carry one or more hydroxyl groups. Preferred examples of these are the α-hydroxy-$C_8$-$C_{18}$-carboxylic acids as well as 12-hydroxystearic acid.

The amount employed here is 0.1-15 wt. %, preferably 0.5-10 wt. %, particularly preferably 1-5 wt. %, in each case based on the total composition.

Fatty alcohols which can be employed are saturated, mono- or polyunsaturated, branched or unbranched fatty alcohols having 6-30, preferably 10-22 and very particularly preferably 12-22 carbon atoms. Dodecanol, -decanol, octanol, octenol, dodecenol, decenol, octadienol, dodecadienol, decadienol, oleyl alcohol, erucyl alcohol, ricinoleyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol as well as guerbet alcohols, e.g. octyldodecanol and hexyldecanol, can be employed e.g. in the context of the invention.

Waxes are often used for stick formulations. Naturally occurring or synthetic waxes which can be employed according to the invention are solid paraffins or isoparaffins, plant waxes, such as candelilla wax, carnauba wax, esparto grass wax, Japan wax, cork wax, sugar cane wax, ouricury wax, montan wax, sunflower wax, fruit waxes and animal waxes, such as e.g. beeswaxes and other insect waxes, spermaceti, shellac wax, wool wax and uropygium fat, and furthermore mineral waxes, such as e.g. ceresin and ozocerite or the petrochemical waxes, such as e.g. petrolatum, paraffin waxes, microwaxes of polyethylene or polypropylene and polyethylene glycol waxes. It may be advantageous to employ hydrogenated or hardened waxes. Chemically modified waxes, in particular the hard waxes, e.g. montan ester waxes, Sasol waxes and hydrogenated jojoba waxes, can furthermore also be employed.

The triglycerides of saturated and optionally hydroxylated $C_{16-36}$-fatty acids, such as e.g. hardened triglyceride fats (hydrogenated palm oil, hydrogenated coconut oil, hydrogenated castor oil), glyceryl tribehenate or glyceryl tri-12-hydroxystearate, are furthermore suitable, and moreover synthetic whole esters of fatty acids and glycols (e.g. Syncrowachs®) or polyols having 2-6 C atoms, fatty acid monoalkanolamides having a $C_{12-22}$-acyl radical and a $C_{2-4}$-alkanol radical, esters of saturated and/or unsaturated, branched and/or unbranched alkanecarboxylic acids of a chain length of 1 to 80 C atoms and saturated and/or unsaturated, branched and/or unbranched alcohols of a chain length of 1 to 80 C atoms, amongst these e.g. synthetic fatty acid-fatty alcohol esters, such as stearyl stearate or cetyl palmitate, esters of aromatic carboxylic acids, dicarboxylic acids and hydroxycarboxylic acids (e.g. 12-hydroxystearic acid) and saturated and/or unsaturated, branched and/or unbranched alcohols of a chain length of 1 to 80 C atoms, lactides of long-chain hydroxycarboxylic acids and whole esters of fatty alcohols and di- and tricarboxylic acids, e.g. dicetyl succinate or dicetyl/stearyl adipate, and mixtures of these substances, as long as the individual wax components, or their mixture, are solid at room temperature.

It is particularly preferable to choose the wax components from the group consisting of esters of saturated, unbranched alkanecarboxylic acids of a chain length of 14 to 44 C atoms and saturated, unbranched alcohols of a chain length of 14 to 44 C atoms, as long as the wax component or the entirety of the wax components are solid at room temperature. The wax components can be particularly advantageously chosen from the group consisting of $C_{16-36}$-alkyl stearates, $C_{10-40}$-alkyl stearates, $C_{2-40}$-alkyl isostearates, $C_{20-40}$-dialkyl esters of dimer acids, $C_{18-38}$-alkyl hydroxystearoylstearates, $C_{20-40}$-alkyl erucates, and $C_{30-50}$-alkyl-beeswax as well as cetearyl behenate can furthermore be employed. Silicone waxes, for example stearyltrimethylsilane/stearyl alcohol, are also advantageous, where appropriate. Particularly preferred wax components are the esters of saturated, monohydric $C_{20}$-$C_{60}$-alcohols and saturated $C_8$-$C_{30}$-monocarboxylic acids, and a $C_{20}$-$C_{40}$-alkyl stearate which is obtainable under the name Kesterwachs® K82H from Koster Keunen Inc. is particularly preferred. The wax or the wax components should be solid at 25° C., but melt in the range of 35-95° C., a range of 45-85° C. being preferred.

Naturally occurring, chemically modified and synthetic waxes can be employed by themselves or in combination.

The wax components are contained in an amount of 0.1 to 40 wt. %, based on the total composition, preferably 1 to 30 wt. % and in particular 5-15 wt. %.

The compositions used according to the invention can furthermore comprise at least one nonpolar or polar liquid oil, which can be naturally occurring or synthetic. The polar oil component can be chosen from plant oils, e.g. sunflower oil, olive oil, soya oil, rape oil, almond oil, jojoba oil and the volatile contents of coconut oil, as well as synthetic triglyceride oils, from ester oils, that is to say the esters of $C_{6-30}$-fatty acids with $C_{2-30}$-fatty alcohols, from dicarboxylic acid esters, such as di-n-butyl adipate, di-(2-ethylhexyl) adipate and di-(2-ethylhexyl) succinates, as well as diol esters, such as ethylene glycol dioleate and propylene glycol di(2-ethylhexanoate), from symmetric, unsymmetric or cyclic esters of carbonic acid with fatty alcohols, for example described in DE-OS 197 56 454, glycerol carbonate or dicaprylyl carbonate (Cetiol® CC), from mono-, di- and tri-fatty acid esters of saturated and/or unsaturated linear and/or branched fatty acids with glycerol, from branched alkanols, e.g. guerbet alcohols with a single branching on carbon atom 2, such as 2-hexyldecanol, 2-octyldodecanol, isotridecanol and isohexadecanol, from alkanediols, e.g. the vicinal diols obtainable from epoxyalkanes having 12-24 C atoms by ring-opening with water, from ether alcohols, e.g. the monoalkyl ethers of glycerol, of ethylene glycol, of 1,2-propylene glycol or of 1,2-butanediol, from dialkyl ethers having in each case 12-24 C atoms, e.g. the alkyl methyl ethers or di-n-alkyl ethers having in each case a total of 12-24 C atoms, in particular di-n-octyl ether (Cetiol® OE ex Cognis), as well as from addition products of ethylene oxide and/or propylene oxide on mono- or polyhydric $C_{3-20}$-alkanols, such as butanol and glycerol, e.g. PPG 3-myristyl ether (Witconol® APM), PPG 14-butyl ether (Ucon Fluid® AP), PPG 15-stearyl ether (Arlamol® E), PPG 9-butyl ether (Breox® B25) and PPG 10-butanediol (Macol® 57). The non-polar oil component can be chosen from liquid paraffin oils, isoparaffin oils, e.g. isohexadecane and isoeicosane, from synthetic hydrocarbons, e.g. 1,3-di-(2-ethyl-hexyl)-cyclohexane (Cetiol® S), and from volatile and non-volatile silicone oils, which can be cyclic, such as e.g. decamethylcyclopentasiloxane and dodecamethylcyclohexasiloxane, or linear, e.g. linear dimethylpolysiloxane, commercially obtainable e.g. under the name Dow Corning® 190, 200, 244, 245, 344 or 345 and Baysilon® 350 M.

The compositions used according to the invention can furthermore comprise at least one water-soluble alcohol. According to the invention, water-solubility is understood as meaning that at least 5 wt. % of the alcohol can be dissolved to give a clear solution at 20° C. or—in the case of long-chain or polymeric alcohols—can be brought into solution by heating the solution to 50° C. to 60° C. Monohydric alcohols, such as e.g. ethanol, propanol or isopropanol, are suitable, depending on the presentation form. Water-soluble polyols are furthermore suitable. These include water-soluble diols, triols and alcohols of higher functionality, as well as polyethylene glycols. Suitable diols are $C_2$-$C_{12}$-diols, in particular 1,2-propylene glycol, butylene glycols, such as e.g. 1,2-butylene glycol, 1,3-butylene glycol and 1,4-butylene glycol, hexanediols, such as e.g. 1,6-hexanediol. Glycerol and in particular diglycerol and triglycerol, 1,2,6-hexanetriol and the polyethylene glycols (PEG) PEG-400, PEG-600, PEG-1000, PEG-1550, PEG-3000 and PEG-4000 are furthermore preferably suitable.

The amount of alcohol or alcohol mixture in the compositions according to the invention is 1-50 wt. %, and preferably 5-40 wt. %, based on the total composition. Both one alcohol and a mixture of several alcohols can be employed according to the invention.

The compositions used according to the invention can be substantially anhydrous, that is to say comprise a maximum of 5 wt. %, preferably a maximum of 1 wt. % of water. In water-containing presentation forms, the water content is 5-98 wt. %, preferably 10-90 and particularly preferably 15-85 wt. %, based on the total composition.

The compositions used according to the invention can furthermore comprise at least one hydrophilically modified silicone. They render possible formulation of highly transparent compositions, reduce the tackiness and leave behind a fresh skin sensation. According to the invention, hydrophilically modified silicones are understood as meaning polyorganosiloxanes with hydrophilic substituents which cause the water-solubility of the silicones. According to the invention, water-solubility is understood as meaning that at least 2 wt. % of the silicone modified with hydrophilic groups dissolves in water at 20° C. Corresponding hydrophilic substituents are, for example, hydroxyl, polyethylene glycol or polyethylene glycol/polypropylene glycol side chains as well as ethoxylated ester side chains. Hydrophilically modified silicone copolymers, in particular dimethicone copolyols, which are on the market, for example, from Wacker-Chemie under the name Belsil® DMC 6031, Belsil® DMC 6032, Belsil® DMC 6038 or Belsil® DMC 3071 VP, or from Dow Corning under the name DC 2501, are preferably suitable according to the invention. Any desired mixture of these silicones can also be employed according to the invention. The amount of hydrophilically modified silicone or of alcohol mixture in the compositions used according to the invention is 0.5-10 wt. %, preferably 1-8 wt. % and particularly preferably 2-6 wt. %, based on the total weight of the composition.

In a further preferred embodiment, the skin treatment compositions used according to the invention comprise at least one surface-active substance as an emulsifier or surfactant. Anionic and, in particular, nonionic emulsifiers or surfactants are suitable according to the invention. In order to obtain particularly finely divided dispersions, it is advantageous to employ a combination of nonionic emulsifiers. For nonionic emulsifiers, the HLB value is calculated according to the invention in accordance with the formula HLB=(100−L): 5, wherein L is the weight content of the lipophilic groups, i.e. the fatty alkyl or fatty acyl groups, in percent by weight. Emulsifiers which can be used according to the invention are, for example, addition products of 4 to 30 mol of ethylene oxide and/or 0 to 5 mol of propylene oxide on linear $C_8$-$C_{22}$-fatty alcohols, on $C_{12}$-$C_{22}$-fatty acids and on $C_8$-$C_{15}$-alkylphenols, $C_{12}$-$C_{22}$-fatty acid mono- and diesters of addition products of 1 to 30 mol of ethylene oxide on $C_3$-$C_6$-polyols, in particular on glycerol, ethylene oxide and polyglycerol addition products on methyl glucoside fatty acid esters, fatty acid alkanolamides and fatty acid glucamides, $C_8$-$C_{22}$-alkyl mono- and oligoglycosides and ethoxylated analogues thereof, wherein degrees of oligomerization of 1.1 to 5, in particular 1.2 to 2.0, and glucose as the sugar component are preferred, mixtures of alkyl (oligo)-glucosides and fatty alcohols, e.g. the commercially obtainable product Montanov®68, addition products of 5 to 60 mol of ethylene oxide on castor oil and hardened castor oil, partial esters of polyols having 3-6 carbon atoms with saturated $C_8$-$C_{22}$-fatty acids, sterols. Sterols is understood as meaning a group of steroids which carry a hydroxyl group on C atom 3 of the steroid skeleton and are isolated both from animal tissue (zoosterols) and from plant fats (phytosterols). Examples of zoosterols are cholesterol and lanosterol. Examples of suitable phytosterols are beta-sitosterol, stigmasterol, campesterol and ergosterol. Sterols, the so-called mycosterols, are also isolated from fungi and yeasts phospholipids. By these are understood, above all, the glucose phospholipids, which are obtained e.g. as lecithins and phosphatidylcholines from e.g. egg yolk or plant seeds (e.g. soya beans).

fatty acid esters of sugars and sugar alcohols, such as sorbitol, polyglycerols and polyglycerol derivatives, such as, for example, polyglycerol poly-12-hydroxystearate (commercial product Dehymuls® PGPH), linear and branched $C_8$-$C_{30}$-fatty acids and Na, K, ammonium, Ca, Mg and Zn salts thereof, wool wax alcohols, polysiloxanes/polyalkyl polyether copolymers and corresponding derivatives, mixed esters of pentaerythritol, fatty acids, citric acid and fatty alcohol according to DE 1165574 and/or mixed esters of fatty acids having 6 to 22 carbon atoms, methylglucose and polyols, preferably glycerol or polyglycerol, polyalkylene glycols.

According to the invention, it may also be advantageous to employ commercially available emulsifying mixtures, such as e.g. Plantacare® PS 10, a fatty alcohol ether-sulfate/alkyl polyglucoside mixture, or Cutina® KD 16 V, a $C_{16}$-$C_{18}$-fatty acid mono/diglyceride/potassium stearate mixture.

A further preferred embodiment of the invention is characterized in that it comprises at least one lipophilic coemulsifier. The use of coemulsifiers contributes towards the formation of particularly finely divided dispersions. Suitable lipophilic coemulsifiers are in principle emulsifiers having an HLB value of 1-10. Coemulsifiers which can be used are, for example:

linear saturated $C_8$-$C_{24}$-alcohols, e.g. cetyl alcohol, stearyl alcohol, arachidyl alcohol, behenyl alcohol or mixtures of these alcohols, ethoxylated alcohols and carboxylic acids having 8-24 C atoms, which have an HLB value of 1-8, propoxylated alcohols and carboxylic acids having 8-24 C atoms, partial esters of a $C_3$-$C_6$-polyol and saturated and/or unsaturated branched and/or unbranched $C_8$-$C_{24}$-fatty acids, e.g. the monoglycerides of palmitic, stearic acid and oleic acid, the sorbitan mono- and/or diesters, in particular those of myristic acid, palmitic acid, stearic acid or of mixtures of these fatty acids, and also the monoesters of trimethylolpropane, erythritol or pentaerythritol and saturated $C_{14}$-$C_{22}$-fatty acids, polyglycerol esters of saturated and/or unsaturated, branched and/or unbranched $C_8$-$C_{24}$-alkanecarboxylic acids having up to 10 glycerol units and a degree of esterification of 1-10, mono- and/or polyglycerol ethers of saturated and/or unsaturated, branched and/or unbranched $C_8$-$C_{30}$-alcohols having up to 10 glycerol units and a degree of etherification of 1-10, propylene glycol esters of saturated and/or unsaturated, branched and/or unbranched $C_8$-$C_{24}$-alkanecarboxylic acids, methylglucose esters of saturated and/or unsaturated, branched and/or unbranched $C_8$-$C_{24}$-alkanecarboxylic acids, polyglycerol methylglucose esters of saturated and/or unsaturated, branched and/or unbranched $C_8$-$C_{24}$-alkanecarboxylic acids.

The compositions used according to the invention preferably comprise the emulsifiers in amounts of 0.1 to 25 wt. %, in particular 0.5-15 wt. %, based on the total composition.

In a preferred embodiment, the compositions used according to the invention comprise at least one antiperspirant active compound. Suitable antiperspirant active compounds are water-soluble astringent metallic salts, in particular inorganic and organic salts of aluminum, zirconium and zinc, and any desired mixtures of these salts. According to the invention, water-solubility is understood as meaning a solubility of at least 5 g of active substance per 100 g of solution at 20° C. Alum ($KAl(SO_4)_2 \cdot 12H_2O$), aluminum sulfate, aluminum lactate, sodium aluminum chlorohydroxylactate, aluminum chlorohydroxyallantoinate, aluminum chlorohydrate, aluminum sulfocarbolate, aluminum zirconium chlorohydrate, zinc chloride, zinc sulfocarbolate, zinc sulfate, zirconium chlorohydrate and aluminum zirconium chlorohydrate-glycine complexes, for example, can be used according to the invention. The compositions preferably comprise an astringent aluminum salt, in particular aluminum chlorohydrate, and/or an aluminum-zirconium compound. The antiperspirant active compounds are employed as aqueous solutions in the case of aqueous applications. In anhydrous compositions, the antiperspirant active compounds are employed in solid form. They are contained in the compositions used according to the invention in an amount of 1-40 wt. %, preferably 5-30 wt. % and in particular 10-25 wt. % (based on the amount of active substance in the total composition). Aluminum chlorohydrates are marketed, for example, in powder form as Micro Dry® Utrafine by Reheis, as Chlorhydrol®, in activated form as Reach® 501 by Reheis and in the form of an aqueous solution as Locron® L by Clariant. An aluminum sesquichlorohydrate is available from Reheis under the name Reach® 301. The use of aluminum zirconium tetrachlorohydrex-glycine complexes which are on the market, for example, from Reheis under the name Rezal® 36G, is also particularly advantageous according to the invention.

The compositions used according to the invention can furthermore comprise additional deodorants. Deodorants which can be employed are fragrances, antimicrobial, antibacterial or germ-inhibiting substances, antioxidants or odor adsorbents (e.g. zinc ricinoleate).

Suitable antimicrobial, antibacterial or germ-inhibiting substances are, in particular, organohalogen compounds as well as -halides, quaternary ammonium compounds, a number of plant extracts and zinc compounds. Halogenated phenol derivatives, such as e.g. hexachlorophene or Irgasan DP 300 (triclosan, 2,4,4'-trichloro-2'-hydroxydiphenyl ether), 3,4,4'-trichlorocarbonilide, chlorhexidine (1,1'-hexamethylene-bis-[5-(4-chlorophenyl)]-biguanide), chlorhexidine gluconate, benzalkonium halides and cetylpyridinium chloride. Sodium bicarbonate, sodium phenolsulfonate and zinc phenolsulfonate as well as e.g. the constituents of linden blossom oil can moreover be employed. Substances which have a relatively weak antimicrobial action but have a specific action against the Gram-positive germs responsible for decomposition of perspiration can also be employed as deodorant active compounds. These include many essential oils, such as e.g. clove oil (eugenol), mint oil (menthol) or thyme oil (thymol), as well as terpene alcohols, such as e.g. farnesol. Benzyl alcohol, the esters of aliphatic $C_2$-$C_6$-carboxylic acids or hydroxycarboxylic acids and $C_2$-$C_6$-alcohols or polyols, e.g. triethyl citrate, propylene glycol lactate, polyglycerol caprylate or glycerol triacetate (triacetin), can also be employed as a deodorant active compound. Further antibacterially active deodorants are lantibiotics, glycoglycerolipids, sphingolipids (ceramides), sterols and other active compounds which inhibit adhesion of bacteria to the skin, e.g. glycosidases, lipases, proteases, carbohydrates, di- and oligosaccharide fatty acid esters and alkylated mono- and oligosaccharides. Long-chain diols, e.g. 1,2-alkane-($C_8$-$C_{18}$)-diols, glycerol mono-($C_6$-$C_{16}$)-alkyl ethers or glycerol mono ($C_8$-$C_{18}$)-fatty acid esters, which have a very good skin and mucous membrane tolerability and are active against Corynebacteria, are also suitable.

Antioxidative substances can counteract the oxidative decomposition of the perspiration components and in this way inhibit odor development. Suitable antioxidants are imidazole and imidazole derivatives (e.g. urocanic acid), peptides, such as e.g. D,L-carnosine, D-carnosine, L-carnosine and derivatives thereof (e.g. anserine), carotenoids, carotenes (e.g. α-carotene, β-carotene, lycopene) and derivatives thereof, liponic acid and derivatives thereof (e.g. dihydroliponic acid), aurothioglucose, propylthiouracil and further thio compounds (e.g. thioglycerol, thiosorbitol, thioglycollic acid, thioredoxin, glutathione, cysteine, cystine, cystamine and glycosyl, N-acetyl, methyl, ethyl, propyl, amyl, butyl, lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta, hexa-, heptathionine sulfoximine) in very low tolerated dosages (e.g. pmol/kg to μmol/kg), furthermore metal-chelating agents (e.g. α-hydroxy-fatty acids, EDTA, EGTA, lactoferrin), humic acids, bile acid, bile extracts, catechols, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, tocophereth-5, tocophereth-10, tocophereth-12, tocophereth-18, tocophereth-50, tocophersolan), vitamin A and derivatives (e.g. vitamin A palmitate), coniferyl benzoate of benzoin resin, rutin, rutic acid and derivatives thereof, disodium rutinyl disulfate, cinnamic acid and derivatives thereof, kojic acid, chitosan glycollate and salicylate, butylhydroxytoluene, butylhydroxyanisole, nordihydroguaiac resin acid, nordihydroguaiaretic acid, trihydroxybutyrophenone, uric acid and derivatives thereof, mannose and derivatives thereof, selenium and selenium derivatives (e.g. selenium-methionine), stilbenes and stilbene derivatives (e.g. stilbene oxide, trans-stilbene oxide). Suitable derivatives (salts, esters, sugars, nucleotides, nucleosides, peptides and lipids) and mixtures of these active compounds or plant extracts mentioned which comprise these antioxidants can be employed according to the invention.

Tocopherol and derivatives thereof and carotenoids as well as butylhydroxytoluene/anisole are preferred as lipophilic, oil-soluble antioxidants from this group. Amino acids, e.g. tyrosine and cysteine, and derivatives thereof as well as tanning substances, in particular those of plant origin, are preferred water-soluble antioxidants.

The total amount of antioxidants in the formulations used according to the invention is 0.001-10 wt. %, preferably 0.05-5 wt. % and in particular 0.1-2 wt. %, based on the total formulation.

Complexing substances can also assist the deodorizing action in that they complex the oxidatively catalytically active heavy metal ions (e.g. iron or copper) in a stable manner. Suitable complexing agents are e.g. the salts of ethylenediaminetetraacetic acid or of nitrilotriacetic acid and the salts of 1-hydroxyethane-1,1-diphosphonic acid.

Liquid and gelatinous presentation forms can comprise thickeners, e.g. cellulose ethers, such as hydroxypropylcellulose, hydroxyethylcellulose and methylhydroxypropylcellulose, thickening polymers based on polyacrylates, which can be crosslinked if desired, e.g. the Carbopol types or Pemulen® products, or based on polyacrylamides, or on polyacrylates containing sulfonic acid groups, e.g. Sepigel® 305 or Simulgel® EG, and furthermore inorganic thickeners, e.g. bentonites and hectorites (Laponite®)

The compositions used according to the invention can comprise further cosmetically and dermatologically active substances, such as, for example, inflammation-inhibiting substances, solids chosen from silicas, e.g. Aerosil® types, silica gels, silicon dioxide, clays, e.g. bentonites or kaolin, magnesium aluminum silicates, e.g. talc, boron nitride, titanium dioxide, which can be coated, if desired, optionally modified starches and starch derivatives, cellulose powders and polymer particles, and furthermore protein hydrolysates, vitamins, UV filters, perfume oils, sebostatics, anti-acne active compounds as well as keratolytic agents.

The cosmetic deodorant or antiperspirant compositions which comprise the β-glucuronidase inhibitors used according to the invention, if they are in liquid form, can be applied to flexible and absorbent carriers and made available as deodorant or antiperspirant cloths or sponges. Suitable flexible and absorbent carriers in the context of the invention are e.g. carriers of textile fibers, collagen or polymeric foams. Both naturally occurring fibers, such as cellulose (cotton, linen), silk, wool, regenerated cellulose (viscose, rayon), cellulose derivatives, and also synthetic fibers, such as e.g. polyester, polyacrylonitrile, polyamide fibers or polyolefin fibers or mixtures of such fibers can be used in woven or non-woven form as textile fibers. These fibers can be processed to absorbent cotton pads, non-wovens or to woven fabrics or knitted fabrics. Flexible and absorbent polymeric foams, e.g. polyurethane foams and polyamide foams, are also suitable substrates. The substrates can have one, two, three and more than three layers, wherein the individual layers can be made of the same or different materials. Each substrate layer can have a homogeneous or inhomogeneous structure with, for example, various zones of different density.

Those carrier substrates which can bind at least 10 wt. % of water, based on the dry weight, by adsorption or capillary forces at 20° C. are to be regarded as adsorbent in the context of the invention. However, those carriers which can bind at least 100 wt. % of water by adsorption and capillary forces are preferably suitable. The carrier substrates are treated in a manner in which the absorbent, flexible carrier substrates, preferably of textile fibers, collagen or polymeric foams, are treated or finished with the compositions according to the invention and, if appropriate, dried. In this context, the treatment (finishing) of the carrier substrates can be carried out by any desired processes, e.g. by spraying on, dipping and squeezing off, impregnation or simply by injecting the composition according to the invention into the carrier substrates.

The presentation form as an aerosol is furthermore preferred according to the invention, the cosmetic composition comprising a propellant chosen from propane, butane, isobutane, pentane, isopentane, dimethyl ether, carbon dioxide, dinitrogen oxide, fluorohydrocarbons and fluorochlorohydrocarbons as well as mixtures thereof.

The following examples are intended to illustrate the invention without limiting it thereto.

Recipe examples
Anhydrous surfactant-containing AT sticks
(data in parts by weight)

|  | 1.1 | 1.2 | 1.3 | 1.4 | 1.5 | 1.6 | 1.7 | 1.8 | 1.9 |
|---|---|---|---|---|---|---|---|---|---|
| Silikonol DC ® 245 | 28 | 28 | 23 | 23 | 23 | 38 | 42 | 47 | 31 |
| Eutanol ® G 16 | 10 | — | — | 15 | 10 | — | 10 | — | 10 |
| Cetiol ® OE | — | 10 | 15 | — | — | — | — | — | — |
| Ucon Fluid ® AP | 5 | 5 | 5 | 5 | 5 | 5 | 5 | 5 | 5 |
| Cutina ® HR | 6 | 6 | 6 | 6 | 6 | 6 | 2 | 5 | 6 |
| Lorol ® C 18 | 20 | 20 | 20 | — | 20 | 20 | — | — | 20 |
| Lanette ® O | — | — | — | 20 | — | — | 10 | 12 | — |

-continued

Recipe examples
Anhydrous surfactant-containing AT sticks
(data in parts by weight)

| | 1.1 | 1.2 | 1.3 | 1.4 | 1.5 | 1.6 | 1.7 | 1.8 | 1.9 |
|---|---|---|---|---|---|---|---|---|---|
| Eumulgin ® B 3 | 3 | 3 | 3 | 3 | 3 | 3 | 3 | 3 | — |
| Cutina ® E 24 PF | — | — | — | — | 5 | — | — | — | — |
| Aluminum chlorohydrate | 20 | 20 | 20 | 20 | 20 | 20 | 20 | — | — |
| Talc | 7.9 | 7 | 7.9 | 7.9 | 7.95 | 7.8 | 7.9 | 27 | 26.5 |
| Isopulegol | 0.1 | — | — | — | — | — | — | — | — |
| Eugenyl glucoside | — | 1.0 | — | — | — | — | — | — | — |
| Raspberry ketone glucoside | — | — | 0.1 | — | — | — | — | — | — |
| Zinc gluconate | — | — | — | 0.1 | — | — | — | — | — |
| Zinc pyrrolidonecarboxylic acid | — | — | — | — | 0.05 | — | — | — | — |
| Zinc cocoyl ether-sulfate | — | — | — | — | — | 0.2 | — | — | — |
| Zinc glycinate monohydrate | — | — | — | — | — | — | 0.1 | — | — |
| Ascorbyl glucoside | — | — | — | — | — | — | — | 1.0 | — |
| 2-Ethylhexyl glycerol ether | — | — | — | — | — | — | — | — | 1.5 |

Sprayable, translucent antiperspirant microemulsions (data in wt. %)

| | 2.1 | 2.2 | 2.3 | 2.4 | 2.5 | 2.6 | 2.7 | 2.8 | 2.9 |
|---|---|---|---|---|---|---|---|---|---|
| Plantaren ® 1200 | 1.71 | 1.71 | — | 1.71 | 1.71 | — | 1.71 | 1.71 | 1.71 |
| Plantaren ® 2000 | 1.14 | 1.39 | 2.40 | 1.14 | 1.39 | 2.40 | 1.14 | 1.39 | 1.39 |
| Glycerol monooleate | 0.71 | 0.71 | — | 0.71 | 0.71 | — | 0.71 | 0.71 | 0.71 |
| Dioctyl ether | 4.00 | 4.00 | 0.09 | 4.00 | 4.00 | 0.09 | 4.00 | 4.00 | 4.00 |
| Octyldodecanol | 1.00 | 1.00 | 0.02 | 1.00 | 1.00 | 0.02 | 1.00 | 1.00 | 1.00 |
| Perfume oil | 1.00 | 1.00 | 1.00 | 1.00 | 1.00 | 1.00 | 1.00 | 1.00 | 1.00 |
| Aluminum chlorohydrate | 8.00 | 5.00 | 5.00 | — | — | — | 8.00 | 5.00 | 5.00 |
| 1,2-Propylene glycol | 5.00 | 5.00 | — | 5.00 | 5.00 | — | 5.00 | 5.00 | 5.00 |
| Glycerol | — | — | 5.00 | — | — | 5.00 | — | — | — |
| Phenoxyethanol | 1.0 | — | — | — | — | — | — | — | — |
| Zinc lactate | — | 0.2 | — | — | — | — | — | — | — |
| Hinokitiol | — | — | 0.01 | — | — | — | — | — | — |
| Copper gluconate | — | — | — | 0.1 | — | — | — | — | — |
| Potassium lactate | — | — | — | — | 1.0 | — | — | — | — |
| Magnesium glucoheptonate | — | — | — | — | — | 1.7 | — | — | — |
| Glycine | — | — | — | — | — | — | 0.2 | — | — |
| Rosemary acid | — | — | — | — | — | — | 0.01 | — | — |
| Phytic acid | — | — | — | — | — | — | — | 1.0 | — |
| Tripotassium citrate | — | — | — | — | — | — | — | — | 1.0 |
| Water | to 100 | to 100 | to 100 | to 100 | to 100 | to 100 | to 100 | to 100 | to 100 |

| | 2.10 | 2.11 | 2.12 | 2.13 | 2.14 | 2.15 | 2.16 | 2.17 |
|---|---|---|---|---|---|---|---|---|
| Plantaren ® 1200 | 1.71 | 1.71 | — | 1.71 | 1.71 | — | 1.71 | 1.71 |
| Plantaren ® 2000 | 1.14 | 1.39 | 2.40 | 1.14 | 1.39 | 2.40 | 1.14 | 1.39 |
| Glycerol monooleate | 0.71 | 0.71 | — | 0.71 | 0.71 | — | 0.71 | 0.71 |
| Dioctyl ether | 4.00 | 4.00 | 0.09 | 4.00 | 4.00 | 0.09 | 4.00 | 4.00 |
| Octyldodecanol | 1.00 | 1.00 | 0.02 | 1.00 | 1.00 | 0.02 | 1.00 | 1.00 |
| Perfume oil | 1.00 | 1.00 | 1.00 | 1.00 | 1.00 | 1.00 | 1.00 | 1.00 |
| Aluminum chlorohydrate | 8.00 | 5.00 | 5.00 | — | — | — | 8.00 | 5.00 |
| 1,2-Propylene glycol | 5.00 | 5.00 | — | 5.00 | 5.00 | — | 5.00 | 5.00 |
| Glycerol | — | — | 5.00 | — | — | 5.00 | — | — |
| Bacocalmine | 1.0 | — | — | — | — | — | — | — |
| Ederline H | — | 0.5 | — | — | — | — | — | — |
| Emblica | — | — | 0.05 | — | — | — | — | — |
| Eurol BT | — | — | — | 0.05 | — | — | — | — |
| Lipochroman-6 | — | — | — | — | 0.005 | — | — | — |
| Olive tree stand. dry extract 12% | — | — | — | — | — | 0.05 | — | — |
| Pantrofina PC | — | — | — | — | — | — | 0.5 | — |
| Rosemary extract 8% NC | — | — | — | — | — | — | — | 0.1 |
| Water | to 100 | to 100 | to 100 | to 100 | to 100 | to 100 | to 100 | to 100 |

| | 2.18 | 2.19 | 2.20 | 2.21 | 2.22 |
|---|---|---|---|---|---|
| Plantaren ® 1200 | 1.71 | 1.71 | — | 1.71 | 1.71 |
| Plantaren ® 2000 | 1.14 | 1.39 | 2.40 | 1.14 | 1.39 |
| Glycerol monooleate | 0.71 | 0.71 | — | 0.71 | 0.71 |
| Dioctyl ether | 4.00 | 4.00 | 0.09 | 4.00 | 4.00 |
| Octyldodecanol | 1.00 | 1.00 | 0.02 | 1.00 | 1.00 |

| Sprayable, translucent antiperspirant microemulsions (data in wt. %) | | | | | |
|---|---|---|---|---|---|
| Perfume oil | 1.00 | 1.00 | 1.00 | 1.00 | 1.00 |
| Aluminum chlorohydrate | 8.00 | 5.00 | 5.00 | — | — |
| 1,2-Propylene glycol | 5.00 | 5.00 | — | 5.00 | 5.00 |
| Glycerol | — | — | 5.00 | — | — |
| Zinc sulfate | 0.1 | — | — | — | — |
| MgCl$_2$.7 H$_2$O | — | 0.1 | — | — | — |
| Willowherb extract | — | — | 0.5 | — | — |
| Tegodeo Lys | — | — | — | 0.1 | — |
| Herbasol MPE Deo | — | — | — | — | 0.1 |
| Water | to 100 | to 100 | to 100 | to 100 | to 100 |

| Soap-containing sticks (data in wt. %) | | | | | | | |
|---|---|---|---|---|---|---|---|
| | 3.1 | 3.2 | 3.3 | 3.4 | 3.5 | 3.6 | 3.7 |
| Ethanol | 22.5 | 22.5 | 22.5 | 22.5 | 22.5 | 22.5 | 22.5 |
| Cutina ® FS 45 | 4.4 | 4.4 | 4.4 | 4.4 | 4.4 | 4.4 | 4.4 |
| 1,3 Butanediol | 31.7 | 31.7 | 31.7 | 31.7 | 31.7 | 31.7 | 31.7 |
| 1,2 Propylene glycol | 21.0 | 21.0 | 21.0 | 21.0 | 21.0 | 21.0 | 21.0 |
| Eutanol ® G | 2.0 | 2.0 | 2.0 | 2.0 | 2.0 | 2.0 | 2.0 |
| Aethoxal ® B | 3.0 | 3.0 | 3.0 | 3.0 | 3.0 | 3.0 | 3.0 |
| Creamophor ® RH 455 | 0.05 | 0.05 | 0.05 | 0.05 | 0.05 | 0.05 | 0.05 |
| NaOH 45% strength | 1.44 | 1.44 | 1.44 | 1.44 | 1.44 | 1.44 | 1.44 |
| Phenoxyethanol | 1.0 | 1.0 | 1.0 | 1.0 | 1.0 | 1.0 | 1.0 |
| Sensiva ® SC 50 | 0.3 | 0.3 | 0.3 | 0.3 | 0.3 | 0.3 | 0.3 |
| Perfume oil | 2.0 | 2.0 | 2.0 | 2.0 | 2.0 | 2.0 | 2.0 |
| Eugenyl glucoside | 1.0 | — | — | — | — | — | — |
| Ascorbyl phosphate Na | — | 0.4 | — | — | — | — | — |
| Dermawhite ® HS LS 8110 B | — | — | 1.0 | — | — | — | — |
| Green tea extract | — | — | — | 0.015 | — | — | — |
| Dequest ® 2066 | | | | 0.2 | | | |
| Ferulan ® Proactiv | — | — | — | — | 0.1 | — | — |
| Caffeic acid | | | | | | 0.02 | |
| Japan tea extract | — | — | — | — | — | — | 0.2 |
| Phenylethyl alcohol | — | — | — | — | — | — | 1.0 |
| Water dist. | to 100 | to 100 | to 100 | to 100 | to 100 | to 100 | to 100 |

| Deodorant in a pump atomizer (data in wt. %) | | | | | | | | |
|---|---|---|---|---|---|---|---|---|
| | 4.1 | 4.2 | 4.3 | 4.4 | 4.5 | 4.6 | 4.7 | 4.8 |
| Ethanol 96% (DEP denatured) | 55.0 | 55.0 | 55.0 | 55.0 | 55.0 | 55.0 | 55.0 | 55.0 |
| Triethyl citrate | 3.0 | 3.0 | 3.0 | 3.0 | 3.0 | 3.0 | 3.0 | 3.0 |
| Cremophor ® RH 455 | 0.5 | 0.5 | 0.5 | 0.5 | 0.5 | 0.5 | 0.5 | 0.5 |
| Eucarol ® AGE-EC | 1.0 | — | — | — | — | — | — | — |
| Eucarol ® AGE-ET | — | 0.2 | — | — | — | — | — | — |
| Eucarol ® AGE-SS | — | — | 1.0 | — | — | — | — | — |
| Mycosporine-like amino acids (MAA) which can be isolated from marine organisms | — | — | — | 0.05 | — | — | — | — |
| Dequest ® 2016 D | — | — | — | — | 0.1 | — | — | — |
| Trilon ® M | — | — | — | — | — | 0.2 | — | — |
| Flavonoid Complex SC | — | — | — | — | — | — | 0.5 | — |
| ARP 100 | — | — | — | — | — | — | — | 1.0 |
| Perfume oil | 1.0 | 1.0 | 1.0 | 1.0 | 1.0 | 1.0 | 1.0 | 1.0 |
| Water | to 100 | to 100 | to 100 | to 100 | to 100 | to 100 | to 100 | to 100 |

| Anhydrous deodorant spray (data in wt. %) | | |
|---|---|---|
| | 6.1 | 6.2 |
| 2-Octyldodecanol | 0.5 | 0.5 |
| Ethanol 99% (DEP denatured) | 39 | 39.45 |
| Naringin | 0.05 | — |
| Hinokitiol | — | 0.01 |
| n-Butane | to 100 | to 100 |

| Antiperspirant roll-on (data in wt. %) | | | | | | |
|---|---|---|---|---|---|---|
| | 5.1 | 5.2 | 5.3 | 5.4 | 5.5 | 5.6 |
| Ethanol 96% (DEP denatured) | 30.0 | 30.0 | 30.0 | 30.0 | 30.0 | 30.0 |
| Mergital ® CS 11 | 2.0 | 2.0 | 2.0 | 2.0 | 2.0 | 2.0 |
| Eumulgin ® B 3 | 2.0 | 2.0 | 2.0 | 2.0 | 2.0 | 2.0 |
| Aluminum chlorohydrate | 20.0 | 20.0 | 20.0 | 20.0 | 20.0 | 20.0 |
| Hydroxyethylcellulose | 0.5 | 0.5 | 0.5 | 0.5 | 0.5 | 0.5 |
| Dermosoft ® HMA | 0.5 | — | — | — | — | — |
| Galactaric acid | — | 0.1 | — | — | — | — |
| Salicylic acid | — | — | 0.4 | — | — | — |
| Tinocare ® CP | — | — | — | 0.5 | — | — |
| Paraguayan tea extract (Dragoco) | — | — | — | — | 0.015 | — |
| Spirulina SPHM 3002 | — | — | — | — | — | 0.2 |
| Perfume oil | 0.8 | 0.8 | 0.8 | 0.8 | 0.8 | 0.8 |
| Water | to 100 | to 100 | to 100 | to 100 | to 100 | to 100 |

| Antiperspirant spray of the suspension type (data in wt. %) | | |
|---|---|---|
| | 6.1 | 6.2 |
| DC-245 | 10.0 | 10.0 |
| Isopropyl myristate | 5.0 | 5.0 |
| Aluminum chlorohydrate powder | 5.0 | 5.0 |
| Aerosil ® R 972 | 2.0 | 2.0 |
| Geraniol-7 EO | 0.5 | — |
| Alutrat ® | — | 2.0 |
| n-Butane | ad 100 | ad 100 |

Antiperspirant Cloths

For the embodiment according to the invention as an antiperspirant cloth, a single-layered substrate of 100% viscose with a weight per unit area of 50 g/m$^2$ was charged with in each case 75 g of emulsion examples 2.1 or 2.2 or 2.3 per square meter or with in each case 75 g of the solution examples 4.1 or 4.2, cut into cloths of suitable size and packed in sachets.

| List of the raw materials employed | | |
|---|---|---|
| DC ® 245 | Cyclopentasiloxane | Dow Corning |
| Actiplex ES | Mucic acid, galactaric acid | Creaderm SA |
| Aethoxal ® B | PPG-5-laureth-5 | Cognis |
| Alutrat ® | Aluminum citrate | Vevy |
| ARP 100 | Extract from the berries of Saw Palmetto | Greentech/Rahn |
| Bacocalmine | Bacopa Monniera Extract, Aqua, PEG-8, Hydroxyethylcellulose, Ascorbic Acid | Sederma |
| Cetiol ® OE | DICAPRYLYL ETHER | Cognis |
| Cooolact P | Isopulegol | Takasago |
| Cremophor ® RH | Hydrogenated castor oil with 40 | BASF |

-continued

| List of the raw materials employed | | |
|---|---|---|
| 455 | EO, containing propylene glycol | |
| Cutina ® FS 45 | Fatty acid mixture of palmitic and stearic acid | Cognis |
| Cutina ® E 24 PF | PEG-20 GLYCERYL STEARATE | Cognis |
| Cutina ® HR | Hardened castor oil | Cognis |
| Dequest ® 2016 D | 1-Hydroxyethane-1,1-diphosphonic acid tetrasodium salt, active substance 84% | Solutia (Monsanto) |
| Dequest ® 2066 | Diethylenetriaminepenta (methylene-phosphonic acid) sodium salt, active acid 45-49% | Solutia (Monsanto) |
| Dermawhite ® HS LS 8110 B | Mannitol and Arginine HCl and Phenylalanine and Disodium EDTA and Sodium Citrate and Kojic Acid and Citric Acid and Yeast Extract | Laboratoires Sérobiologiques |
| Dermosoft HMA | p-Hydroxymandelic acid sodium salt, active substance 95-96% | Dr. Straetmans |
| Ederline H | PEG 40-Hydrogenated Castor Oil, PPG-2 Ceteareth-9, Apple Extract | Impag |
| Emblica | Naturally occurring active compound combination from *Phyllanthus emblica* | Merck KGaA |
| Eucarol ® AGE-EC-UP | Disodium Cocopolyglucose Citrate, 30% active substance in water | Cesalpinia Chemicals |
| Eucarol ® AGE-ET-UP | Disodium Cocopolyglucose Tartrate, 30% active substance in water | Cesalpinia Chemicals |
| Eucarol ® AGE-SS | Disodium Cocopolyglucose Sulfosuccinate, 45% active substance in water | Cesalpinia Chemicals |
| Eumulgin ® B 3 | CETEARETH-30 | Cognis |
| Eurol BT | Olive leaf extract | Impag |
| Eutanol ® G 16 | 2-Hexyldecanol | Cognis |
| Ferulan ® Proactiv | Ethoxydiglycol and Glycerin and Ferulic Acid and PEG-40 Hydrogenated Castor Oil and *Oryza Sativa* (Rice) Bran Oil | GfN |
| Flavonoid complex SC | Water, Butylene Glycol, Gingko Biloba Leaf Extract, Phenoxyethanol, Methyl Paraben, Ethyl Paraben, Propyl Paraben, Butyl Paraben, Isobutyl Paraben, approx. 2% flavonoid content | Cosmetochem |
| Givobio GCU | Copper gluconate | Seppic |
| Green tea extract | Pulverulent | Dragoco |
| Herbasol MPE Deo | PEG-40 Hydrogenated Castor Oil, Hyssop Extract, Clove Extract, Water | Cosmetochem |
| Japan tea extract H-G | Pulverulent | Dragoco |
| Lanette ® O | Cetyl/stearyl alcohol in a ratio of 1:1 | Cognis |
| Lipochroman-6 | Dimethylmethoxy Chromanol | Lipotec S.A. |
| Lorol ® C 18 | Stearyl alcohol | Cognis |
| Paraguayan tea extract | Pulverulent | Dragoco |
| Mergital ® CS 11 | CETEARETH-11 | Cognis |
| Olive tree stand. dry extract 12% | Olea europeaea Leaf, 55-65%, 33-43% Maltodextrin, 2% Silica | Cognis |
| Plantaren ® 1200 | LAURYL GLUCOSIDE, approx. 50% active substance | Cognis |
| Plantaren ® 2000 | DECYL GLUCOSIDE, approx. 50% active substance | Cognis |
| Purasal P Hipure 60 | Potassium lactate | Purac America |
| Rosemary extract 8% NC (−) | Rosemary extract water-soluble powder with standard amount of 5% rosemary acid, 3% apigenin 7-glycoside | Dr. Marcus |
| Sensiva ® SC 50 | 2-Ethylhexyl glycerol ether | Schülke & Mayr |
| *Spirulina* SPHM 3002 | Aqueous extract of *Spirulina platensis* enriched with magnesium | IGV GmbH, Institute of Cereals |

-continued

| | List of the raw materials employed | |
|---|---|---|
| Tegodeo Lys | Zinc ricinoleate, propylene glycol, lysine, 20% water | Processing, Berghoz-Rehbrücke Goldschmidt Degussa |
| Tinocare ® CP | Phosphonomethylated chitosan | Ciba |
| Trilon A | Nitrilotriacetic acid 3 Na | BASF |
| Trilon B | EDTA-4 Na | BASF |
| Trilon ® M | Methylglycinediacetic acid trisodium salt, active substance 39-41% | BASF |
| Ucon Fluid ® AP | PPG-14 BUTYL ETHER | Amerchol (Union Carbide) |
| Willowherb Extract | | Dragoco |

Investigation of the inhibitory action of the β-glucuronidase inhibitors (in vitro)

Since the skin-relevant β-glucuronidase was not available, a commercially available β-glucuronidase (Sigma) (EC 3.2.1.31) from *E. coli* served as the model enzyme for testing the inhibitory action of the inhibitors used according to the invention. The tests were carried out with the β-glucuronidase enzyme assay product no. G-7396 from Sigma in accordance with the instructions in the Sigma Quality Control Test Procedure datasheet.

For the evaluation, the phenolphthalein formed from the substrate phenolphthalein glucuronide by β-glucuronidase was determined spectrophotometrically ($\lambda$=540 nm).

The reaction solutions of 300 μl, which were temperature-controlled at a reaction temperature of 37° C., comprised 30 mM potassium phosphate buffer with 0.04% of albumin (pH 6.8), 0.5 mM phenolphthalein glucuronide (substrate) and a starting concentration of 40 U/ml (=12 U) of β-glucuronidase. The unit U of the enzyme activity was defined such that 1 U of β-glucuronidase hydrolyses 1.0 μmol of phenolphthalein glucuronide per minute at pH 6.8 and 37° C.

The reaction was started by addition of the enzyme and and incubation was carried out for 30 min at 37° C. The reaction was then stopped with 3.5 times the volume of a 200 mM glycine solution of pH 10.4. In the photometric end point determination, the amount of phenolphthalein liberated was determined at the wavelength of $\lambda$=540 nm and at 37° C.

In batches with inhibitor, 0.2 ml of the appropriately concentrated reagents and 0.1 ml of the inhibitor, dissolved in water, were mixed. In each case a concentration series of the inhibitor was tested here. The absorption (A) here is a measure of the activity of the enzyme ($\Delta A$). The activity of the enzyme in the absence of an inhibitor ($\Delta A_1$) was set at 100% as the reference. Under analogous conditions, the activities were determined in the presence of an inhibitor ($\Delta A_2$). The inhibitory action of the inhibitor was shown as the residual activity of the enzyme activity, calculated in accordance with the equation 100%−($\Delta A_2$)/($\Delta A_1$)%.

The results are listed in the following tables.

| Concentration in the test [%] | 0.00008 | 0.0008 | 0.0005 | 0.01 | 0.10 | 0.50 | 1.00 | 2.00 |
|---|---|---|---|---|---|---|---|---|
| | | | | Residual activity [%] | | | | |
| Actiplex ES | | | | 97 | 1 | | 0 | |
| Alutrat | | | | 94 | 86 | | 56 | |
| ARP 100 | | | | 103 | 82 | | 16 | |
| Ascorbyl phosphate Na | | | | 100 | 95 | | 40 | 46 |
| Coolact P | | | | | | 184 | 38 | |
| Dequest 2016D | | | | 99 | 95 | | 52 | |
| Dequest 2066 | | | | 89 | 86 | | 63 | 23 |
| Dermawhite HS LS 8110 B | | | | 85 | 81 | | 58 | |

| Test concentration [%] | 0.001 | 0.005 | 0.008 | 0.01 | 0.05 | 0.10 | 0.50 | 1.00 | 2.00 |
|---|---|---|---|---|---|---|---|---|---|
| | | | | | Residual activity [%] | | | | |
| Dermosoft HMA | | | | 110 | | 99 | | 56 | |
| Eucarol AGE SS | | | | 69 | | 73 | | 54 | |
| Eucarol | | | | 59 | | 61 | | 54 | |

-continued

The results are listed in the following tables.

| | | | | | | | | | | | | |
|---|---|---|---|---|---|---|---|---|---|---|---|---|
| AGE/EC/UP Eucarol | | | 67 | | 69 | | n.d. | | | | | |
| AGE/ET/UP Eugenyl Glucoside | | | | | 53 | | 12 | | | | | |
| Ferulan Proactive | | | 57 | | 58 | | 49 | | | | | |
| Flavonoid Complex SC | | | 87 | | 27 | | 6 | | | | | |
| Geraniol+7EO | | | 104 | | 170 | | 58 | 15 | | | | |
| Givobio GCU | | | 81 | | 50 | | n.d. | | | | | |
| Magnesium glucoheptonate | | | 55 | | 50 | | n.d. | | | | | |
| Glycine | | | 95 | | 91 | 70 | 52 | 32 | | | | |
| Green tea extract | | | 16 | | n.d. | | n.d. | | | | | |
| Hinokitiol (DMSO) | 112 | | 156 | | 30 | | 2 | | | | | |
| Jap. tea extract H-G | | | | | 42 | n.a. | | | | | | |

| Test concentration [%] | 0.000005 | 0.00005 | 0.00025 |
|---|---|---|---|
| | Residual activity [%] | | |
| CuCl$_2$ × 5H$_2$O | 105 | 39 | 7 |

| Test concentration [%] | 8·10$^{-5}$ | 0.0008 | 0.001 | 0.005 | 0.008 | 0.01 | 0.05 | 0.08 | 0.10 | 0.38 | 0.50 | 1.00 | 2.00 |
|---|---|---|---|---|---|---|---|---|---|---|---|---|---|
| | Residual activity [%] | | | | | | | | | | | | |
| Paraguayan tea extract | | | | | | 24 | | 38 | | | n.d. | | |
| Naringin | | | 103 | | | 94 | | 47 | | | | | |
| Phenoxyethanol | | | | | | | | | | 91 | 6 | | |
| Phytic acid | | | | | | 90 | 86 | 71 | 68 | | 16 | | |
| Zinc lactate | | 77 | | | | 55 | 30 | | | 3 | | | |
| Purasal P Hipure 60 | | | | | | 96 | | 88 | | | 52 | | |
| Raspberry ketone glucoside | | | | | | | | | | 125 | 49 | | |
| Rosemary acid | 86 | 48 | | | | 15 | | 19 | | | | | |
| Spirulina SPHM 3002 | | | | | | 99 | | 95 | | | 52 | | |
| Tinocare CP | | | | | | 100 | | 94 | | | 33 | | |
| Tripotassium citrate | | | | | | 97 | | 86 | | | 47 | | |
| Trilon A | | | | | | 100 | | 90 | | 71 | 59 | 52 | |
| Trilon B | | | | | | 108 | | 86 | | 57 | 51 | 43 | |
| Trilon M | | | | | | 99 | | 91 | | | 55 | | |

| Concentration in the test [%] | 0.005 | 0.01 | 0.025 | 0.05 | 0.10 | 0.25 | 0.50 | 1.00 |
|---|---|---|---|---|---|---|---|---|
| | Residual activity [%] | | | | | | | |
| Zincidone | | 79 | | | 8 | | | 3 |
| Zinc gluconate | | 88 | | | 54 | 3 | | 1 |
| Zinc glycinate monohydrate | 87 | | | 75 | 16 | 1 | 2 | |
| Phenylethyl alcohol | | 121 | | | 227 | | | 49 |
| Alga extract, comprising | 99 | | 86 | 42 | | | | |

-continued

The results are listed in the following tables.

mycosporine-
like amino
acids

We claim:

1. A non-therapeutic method for inhibiting or reducing body odor caused by the hydrolytic decomposition of steroid esters by β-glucuronidase comprising adding to a cosmetic deodorant or antiperspirant composition at least one compound selected from the group consisting of:
monobasic mono-α-hydroxycarboxylic acids having 2-6 carbon atoms and their physiologically acceptable salts,
monobasic polyhydroxycarboxylic acids having 4-8 carbon atoms and 3-7 hydroxyl groups, their intramolecular condensation products as well as ethers thereof with mono-, oligo- and polysaccharides or esters thereof with organic and with inorganic acids as well as the physiologically acceptable salts of these components,
polybasic carboxylic acids which are not hydroxy-substituted and have 3-8 carbon atoms and 2-3 carboxyl groups, their esters with optionally alkyl-substituted mono- and oligosaccharides as well as the physiologically acceptable salts of these components,
polybasic monohydroxycarboxylic acids having 4-8 carbon atoms and 2-3 carboxyl groups, their esters with optionally alkyl-substituted mono- and oligosaccharides as well as the physiologically acceptable salts of these components,
polybasic polyhydroxycarboxylic acids having 4-8 carbon atoms, 2-6 hydroxyl groups and 2-3 carboxyl groups, their esters with optionally alkyl-substituted mono- and oligosaccharides as well as the physiologically acceptable salts of these components,
aromatic carboxylic acids having 6-20 carbon atoms, 1-2 phenyl radicals, 1-6 hydroxyl groups and 1 carboxyl group, as well as physiologically acceptable salts thereof,
amino acids as well as physiologically acceptable salts thereof,
6,7-disubstituted 2,2-dialkylchromanes or -chromenes, phenolic glycosides with a phenoxy radical substituted at least in the para-position, wherein the substituents are chosen from a methoxy, ethoxy, isopropoxy, n-propoxy, vinyl, methylvinyl, 1-propenyl, 2-propenyl, isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, extracts from green tea (*Camellia sinensis*), Paraguayan tea (*Ilex paraguayensis*), Japanese tea (*Camellia japanensis*), from the fruits (berries) of the fan palm or saw palm (Saw Palmetto, *Serenoa repens*), from the leaves of *Gingko biloba*, from apple pips, from the fruits (berries) of *Phyllanthus emblica*, from the leaves of the olive tree (*Olea europaea*), from the bark of the pine tree (*Pinus* Pinaster), from rosemary, from *Bacopa* Monniera, from willow-herb, hyssop, clove, from the blue alga *Spirulina platensis* which has been enriched with magnesium, and from yeast,
flavonoids,
isoflavonoids,
polyphenols,
monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, and
derivatives of phosphonic acid and phosphoric acid chosen from hydroxyethane-1,1-diphosphonic acid, diethylenetriaminepenta (methylenephosphonic acid), myo-inositol-hexaphosphoric acid (phytic acid) and phosphonomethylated chitosan as well as the alkali metal salts of these components, zinc ricinoleate, geraniol-7 EO as well as soluble inorganic salts of copper(II), zinc and magnesium.

2. The method of claim 1 wherein the monobasic mono-α-hydroxycarboxylic acids having 2-6 carbon atoms are chosen from glycollic acid, lactic acid, α-hydroxybutyric acid, α-hydroxyvaleric acid and α-hydroxycaproic acid as well as physiologically acceptable salts thereof.

3. The method of claim 1 wherein the monobasic polyhydroxycarboxylic acids having 4-8 carbon atoms and 3-7 hydroxyl groups are chosen from gluconic acid, galactonic acid, mannonic acid, fructonic acid, arabinonic acid, xylonic acid, ribonic acid and glucoheptonic acid as well as physiologically acceptable salts thereof.

4. The method of claim 1 wherein the intramolecular condensation products of monobasic polyhydroxycarboxylic acids having 4-8 carbon atoms and 3-7 hydroxyl groups, ethers thereof with mono-, oligo- and polysaccharides or esters thereof with organic and with inorganic acids and the physiologically acceptable salts of these components are chosen from ascorbic acid, Na ascorbyl phosphate, Mg ascorbyl phosphate, ascorbyl palmitate, disodium ascorbyl phosphate, disodium ascorbyl sulfate, sodium ascorbate, magnesium ascorbate, ascorbyl stearate, ascorbyl dipalmitate, ascorbyl acetate, potassium ascorbyl tocopheryl phosphate, chitosan ascorbate and ascorbyl glucoside.

5. The method of claim 1 wherein the polybasic carboxylic acids which are not hydroxy-substituted and have 3-8 carbon atoms and 2-3 carboxyl groups as well as the physiologically acceptable salts of these components are chosen from methylglycinediacetic acid and its mono-, di- and tri-alkali metal salts, as well as sulfosuccinic acid and its mono-, di- and tri-alkali metal salts.

6. The method of claim 1 wherein the esters of polybasic carboxylic acids which are not hydroxy-substituted and have 3-8 carbon and 2-3 carboxylic groups with optionally alkyl-substituted mono- and oligosaccharides as well as the physiologically acceptable salts of these components are chosen from $C_8$-$C_{18}$-alkyl-(oligo-)glucosylsulfosuccinic acid and its mono- and di-alkali metal salts.

7. The method of claim 1 wherein the polybasic monohydroxycarboxylic acids having 4-8 carbon atoms and 2-3 carboxyl groups, their esters with optionally alkyl-substituted mono- and oligosaccharides as well as the physiologically acceptable salts of these components are chosen from citric acid, malic acid (hydroxysuccinic acid), hydroxymaleic acid, hydroxyglutaric acid, hydroxyadipic acid, hydroxypimelic acid and hydroxyazelaic acid, $C_8$-$C_{18}$-alkyl (oligo-)glucoside esters thereof as well as the mono-, di- and tri-alkali metal salts and the aluminum salts of these components.

8. The method of claim 1 wherein the polybasic polyhydroxycarboxylic acids having 4-8 carbon atoms, 2-6 hydroxyl groups and 2-3 carboxyl groups, their esters with optionally alkyl-substituted mono- and oligosaccharides as well as the physiologically acceptable salts of these components are chosen from erythraric acid (meso-tartaric acid), L-threaric acid ((+)-tartaric acid), D(−)-tartaric acid, DL-tartaric acid, glucaric acid, galactaric acid (mucic acid), mannaric acid, fructaric acid, arabinaric acid, xylaric acid and ribaric acid, $C_8$-$C_{18}$-alkyl (oligo-)-glucoside esters thereof as well as the mono-, di- and tri-alkali metal salts of these components.

9. The method of claim 1 wherein the aromatic carboxylic acids having 6-20 carbon atoms, 1-2 phenyl radicals, 1-6 hydroxyl groups and 1 carboxyl group, as well as physiologically acceptable salts thereof are chosen from mandelic acid, para-hydroxymandelic acid, rosemary acid, ferulic acid, chlorogenic acid, salicylic acid, 2,3-dihydroxybenzoic acid (pyrocatechic acid), 2,4-dihydroxybenzoic acid (β-resorcylic acid), 2,5-dihydroxybenzoic acid (gentisic acid), 2,6-dihydroxybenzoic acid (γ-resorcylic acid), 3,4-dihydroxybenzoic acid (protocatechuic acid), 3,5-dihydroxybenzoic acid (α-resorcylic acid), gallic acid, the methyl, ethyl isopropyl, propyl, butyl, hexyl, ethylhexyl, octyl, decyl, ethyloctyl, cetyl and stearyl esters and the alkali metal salts of these carboxylic acids.

10. The method of claim 1 wherein the amino acids as well as physiologically acceptable salts thereof are chosen from mycosponine-like amino acids (MAA) which can be isolated from marine organisms, as well as from glycine, senine, tyrosine, threonine, cysteine, asparagines, glutamine, pyroglutamic acid, alanine, valine, leucine, isoleucine, proline, tryptophan, phenylalanine, methionine, aspartic acid, glutamic acid, lysine, arginine and histidine as well as the zinc salts and the acid addition salts of the amino acids mentioned.

11. The method of claim 1 wherein the 6,7-disubstituted 2,2-dialkylchromanes or -chromenes are chosen from the compounds of the general formula (I) or (II)

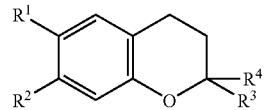

(I)

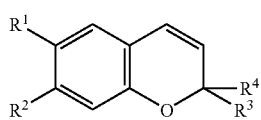

(II)

wherein $R^1$ and $R^2$ independently of one another represent an OH group, a methoxy group or a $CF_3CH_2O$ group and $R^3$ and $R^4$ independently of one another represent a $C_1$-$C_4$-alkyl group.

12. The method of claim 1 wherein the phenolic glycosides with a phenoxy radical substituted at least in the para-position, wherein the substituents are chosen from a methoxy, ethoxy, isopropoxy, n-propoxy, vinyl, methylvinyl, 1-propenyl, 2-propenyl, isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, are chosen from 2-methoxy-4-(2-propenyl)phenyl β-D-glucoside (eugenyl glucoside) and from 4-(γ-ketobutyl)phenyl β-D-glucoside (raspberry ketone glucoside).

13. The method of claim 1 wherein the flavonoids are chosen from naringin, α-glucosylrutin, α-glucosylmyricetin, α-glucosylisoquercetin, α-glucosylguercetin, hesperidin, neohesperidin, rutin, troxerutin, monoxerutin, diosmin, eriodictin, phloricin, neohesperidin dihydrochalcone and apigenin 7-glucoside.

14. The method of claim 1 wherein the isoflavonoids are chosen from daidzein, genistein, glycitein, formononetin, daidzin and genistin.

15. The method of claim 1 wherein the polyphenols are chosen from pyrocatechol, resorcinol, hydroquinone, phloroglucinol, pyrogallol, hexahydroxybenzene, anthocyanidines, flavones, tanning substances (catechols, tannins), usnic acid, acylpolyphenols as well as the derivatives of gallic acid, of digallic acid and of digalloylgallic acid.

16. The method of claim 1 wherein the monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, are chosen from phenoxyethanol, 2-phenylethyl alcohol, 5-hydroxy-2-(hydroxymethyl)-4-pyrone (kojic acid), 5-methyl-2-(1-methylvinyl)-cyclohexan-1-ol (isopulegol) and 2-hydroxy-4-isopropyl-2,4,6-cycloheptatrien-1-one (hinokitiol).

17. A non-therapeutic method for reducing body odor on the skin comprising applying a cosmetic deodorant or antiperspirant composition comprising at least one β-glucuronidase-inhibiting substance selected from the group consisting of:

monobasic mono-α-hydroxycarboxylic acids having 2-6 carbon atoms and their physiologically acceptable salts, monobasic polyhydroxycarboxylic acids having 4-8 carbon atoms and 3-7 hydroxyl groups, their intramolecular condensation products as well as ethers thereof with mono-, oligo- and polysaccharides or esters thereof with organic and with inorganic acids as well as the physiologically acceptable salts of these components, polybasic carboxylic acids which are not hydroxy-substituted and have 3-8 carbon atoms and 2-3 carboxyl groups, their esters with optionally alkyl-substituted mono- and oligosaccharides as well as the physiologically acceptable salts of these components, polybasic monohydroxycarboxylic acids having 4-8 carbon atoms and 2-3 carboxyl groups, their esters with optionally alkyl-substituted mono- and oligosaccharides as well as the physiologically acceptable salts of these components, polybasic polyhydroxycarboxylic acids having 4-8 carbon atoms, 2-6 hydroxyl groups and 2-3 carboxyl groups, their esters with optionally alkyl-substituted mono- and oligosaccharides as well as the physiologically acceptable salts of these components, aromatic carboxylic acids having 6-20 carbon atoms, 1-2 phenyl radicals, 1-6 hydroxyl groups and 1 carboxyl group, as well as physiologically acceptable salts thereof, amino acids as well as physiologically acceptable salts thereof, 6,7-disubstituted 2,2-dialkylchromanes or -chromenes, phenolic glycosides with a phenoxy radical substituted at least in the para-position, wherein the substituents are chosen from a methoxy, ethoxy, isopropoxy, n-propoxy, vinyl, methylvinyl, 1-propenyl, 2-propenyl, isobutenyl, methyl, ethyl, n-propyl, isopropyl, n-butyl, isobutyl, tert-butyl, ketopropyl, β-ketobutyl, γ-ketobutyl, β-ketopentyl, γ-ketopentyl and a δ-ketopentyl radical, extracts from green tea (*Camellia sinensis*), Paraguayan tea (*Ilex paraguayensis*), Japanese tea (*Camellia japanensis*), from the fruits (berries) of the fan palm or saw palm (Saw Palmetto, *Serenoa repens*), from the leaves of *Gingko biloba*, from apple pips, from the fruits (berries) of *Phyllanthus emblica*, from the leaves of the olive tree (*Olea europaea*), from the bark of the pine tree (*Pinus* Pinaster), from rosemary, from *Bacopa Monniera*, from willow-herb, hyssop, clove, from the blue alga *Spirulina platensis* which has been enriched with magnesium, and from yeast, flavonoids, isoflavonoids, polyphenols, monocyclic hydrocarbon compounds having 6-12 carbon atoms, 1-2 hydroxyl groups and oxygen atoms as the only heteroatoms, wherein the ring is formed from 6 or 7 atoms and can be saturated, unsaturated or aromatic, and derivatives of phosphonic acid and phosphoric acid chosen from hydroxyethane-1,1-diphosphonic acid, diethylenetriaminepenta (methylenephosphonic acid), myo-inositol-hexaphosphoric acid (phytic acid) and phosphonomethylated chitosan as well as the alkali metal salts of these components, zinc ricinoleate, geraniol-7 EO as well as soluble inorganic salts of copper(II), zinc and magnesium.

18. The method of claim 17 wherein the β-glucuronidase-inhibiting substance is employed in a sex-specific manner in respect of its concentration and/or nature.

19. The method of claim 17 wherein the arylsulfatase-inhibiting substances are employed for reducing body odor in men.

* * * * *